(12) United States Patent
Rozmaryn

(10) Patent No.: US 7,127,944 B1
(45) Date of Patent: Oct. 31, 2006

(54) SYSTEM AND METHOD FOR MEASURING THE MOTOR STRENGTH OF A HUMAN THUMB OR FINGER

(76) Inventor: Leo M. Rozmaryn, 801 Stonington Rd., Silver Springs, MD (US) 20902

( * ) Notice: Subject to any disclaimer, the term of this patent is extended or adjusted under 35 U.S.C. 154(b) by 0 days.

(21) Appl. No.: 10/717,912

(22) Filed: Nov. 21, 2003

Related U.S. Application Data

(60) Provisional application No. 60/428,277, filed on Nov. 22, 2002.

(51) Int. Cl.
*A61B 5/22* (2006.01)
(52) U.S. Cl. .................................. 73/379.01
(58) Field of Classification Search ............ 73/379.03, 73/379.01, 379.02; 600/595, 587, 554
See application file for complete search history.

(56) References Cited

U.S. PATENT DOCUMENTS

| | | | | |
|---|---|---|---|---|
| 3,897,058 A | * | 7/1975 | Koch | 473/206 |
| 4,236,528 A | * | 12/1980 | Stanec et al. | 600/554 |
| 4,774,966 A | * | 10/1988 | Lemmen | 600/587 |
| 5,163,443 A | * | 11/1992 | Fry-Welch et al. | 600/595 |
| 5,471,996 A | * | 12/1995 | Boatright et al. | 600/595 |
| 5,723,785 A | * | 3/1998 | Manning | 73/379.03 |

* cited by examiner

*Primary Examiner*—Jewel V. Thompson
(74) *Attorney, Agent, or Firm*—Irah H. Donner; Wilmer Cutler Pickering Hale and Dorr LLP

(57) ABSTRACT

A method and apparatus for measuring the strength of a human thumb or finger. Strength can be measured when the thumb or finger moves in at least two substantially opposing directions.

26 Claims, 31 Drawing Sheets

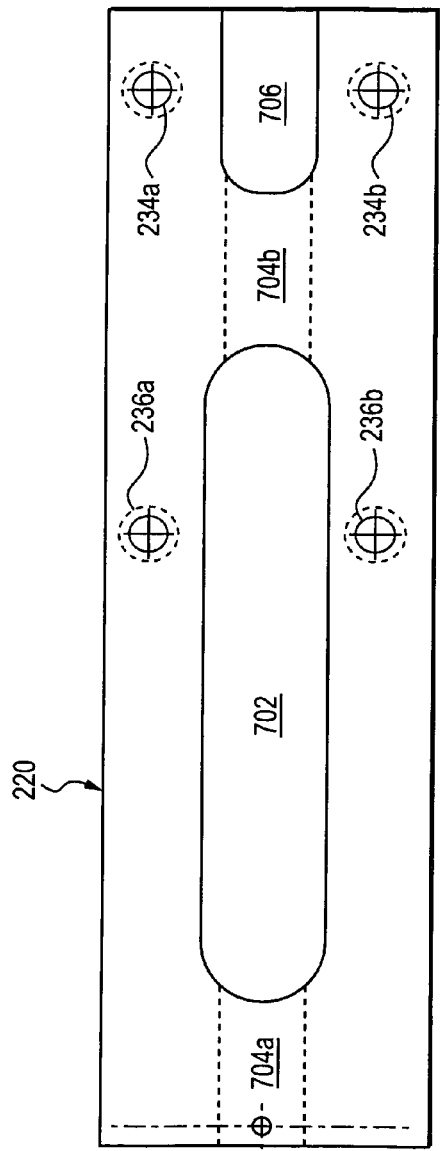
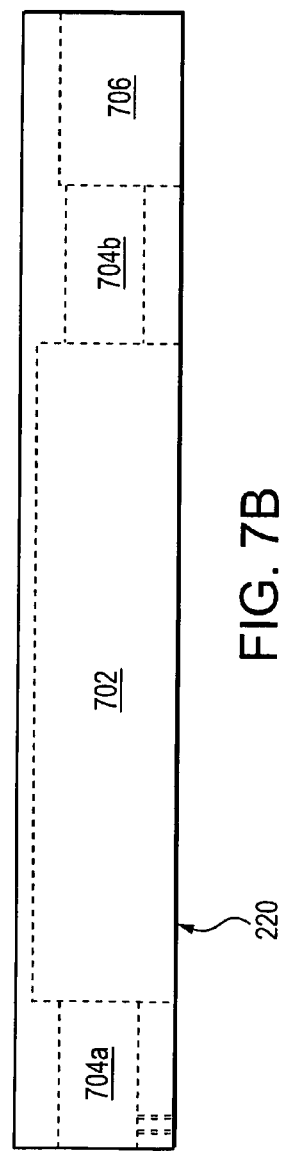
FIG. 7A
FIG. 7B

CHARACTERISTICS OF SUBJECTS: AGE, WEIGHT, SEX FOR RIGHT DOMINANT

MALE-WEIGHT

| AGE | 50-99 | 100-124 | 125-149 | 150-174 | 175-199 | 200-224 | 225-249 | 250-300 | TOTAL |
|---|---|---|---|---|---|---|---|---|---|
| 5 TO 9 | 2 | 12 | 9 | | | | | | 23 |
| 10 TO 14 | | | 9 | 10 | 3 | | | | 22 |
| 15 TO 19 | | | 3 | 16 | 5 | 2 | | | 26 |
| 20 TO 24 | | | 2 | 8 | 11 | 3 | | | 24 |
| 25 TO 29 | | | 2 | 6 | 11 | 1 | 1 | | 21 |
| 30 TO 34 | | | 1 | 7 | 11 | 4 | 1 | 1 | 25 |
| 35 TO 39 | | | 1 | 3 | 9 | 3 | 3 | | 19 |
| 40 TO 44 | | | 1 | 4 | 12 | 5 | 3 | | 25 |
| 45 TO 49 | | | | 2 | 12 | 7 | 2 | | 26 (?) |
| 50 TO 54 | | | 2 | 6 | 10 | 1 | 3 | 1 | 20 (?) |
| 55 TO 59 | | | 3 | 7 | 9 | 3 | 1 | | 23 (?) |
| 60 TO 64 | | | | 8 | 6 | 3 | | | 23 |
| 65 TO 69 | | | 4 | 8 | 6 | 3 | 1 | | 21 |
| TOTAL | 2 | 12 | 38 | 77 | 99 | 32 | 12 | 3 | 275 |

FEMALE-WEIGHT

| AGE | 50-99 | 100-124 | 125-149 | 150-174 | 175-199 | 200-224 | 225-249 | TOTAL | GRAND TOTAL |
|---|---|---|---|---|---|---|---|---|---|
| 5 TO 9 | 2 | 2 | 4 | | | | | 4 | 4 |
| 10 TO 14 | 3 | 17 | 13 | 2 | | | | 24 | 47 |
| 15 TO 19 | | 8 | 15 | 3 | 2 | | | 23 | 45 |
| 20 TO 24 | 1 | 4 | 8 | 6 | 1 | | | 24 | 50 |
| 25 TO 29 | | 8 | 12 | 4 | 6 | | | 25 | 49 |
| 30 TO 34 | | | 10 | 7 | 4 | 2 | | 22 | 43 |
| 35 TO 39 | 1 | 8 | 9 | 8 | 2 | 2 | 1 | 31 | 56 |
| 40 TO 44 | | | 8 | 15 | | 1 | | 21 | 40 |
| 45 TO 49 | | | 4 | 13 | 2 | 1 | | 24 | 49 |
| 50 TO 54 | | | 11 | 6 | 2 | | | 20 | 46 |
| 55 TO 59 | | | 5 | 8 | 3 | | | 20 | 40 |
| 60 TO 64 | | | 5 | 9 | 6 | | | 20 | 43 |
| 65 TO 69 | | | 5 | 9 | 7 | | 1 | 21 | 42 |
| TOTAL | 5 | 45 | 104 | 81 | 33 | 4 | 3 | 275 | 275 |

FIG. 16

JOINT AGE WEIGHT ABDUCTION-RIGHT

| | JOINT AGE WEIGHT ABDUCTION-RIGHT MALE-WEIGHT | | | | | | | | JOINT AGE WEIGHT ABDUCTION-RIGHT FEMALE-WEIGHT | | | | | |
|---|---|---|---|---|---|---|---|---|---|---|---|---|---|---|
| AGE | 50-99 | 100-124 | 125-149 | 150-174 | 175-199 | 200-224 | 225-249 | 250-300 | 50-99 | 100-124 | 125-149 | 150-174 | 175-199 | 200-224 |
| 5 TO 9 | | | | | | | | | | | | | | |
| 10 TO 14 | | 2.6 | 3.1 | | | | | | 1.9 | 2.5 | 2.7 | | | |
| 15 TO 19 | | | 3.8 | 4.9 | 5.3 | | | | | 2.8 | 2.7 | | | |
| 20 TO 24 | | | 4.3 | 6.0 | 6.8 | | | | | 3.7 | 3.0 | 2.6 | | |
| 25 TO 29 | | | | 5.8 | 6.2 | 5.4 | | | | 2.2 | 3.3 | 3.5 | | |
| 30 TO 34 | | | | 4.4 | 5.7 | | | | | | 3.1 | 3.1 | 3.0 | |
| 35 TO 39 | | | | 5.1 | 5.9 | 6.7 | | | | 2.7 | 3.1 | 2.9 | 4.0 | |
| 40 TO 44 | | | | 4.2 | 4.6 | 5.4 | 5.4 | | | | 2.9 | 2.9 | | |
| 45 TO 49 | | | | 4.5 | 5.2 | 6.1 | | | | | 2.9 | 3.0 | | |
| 50 TO 54 | | | | | 5.3 | 6.8 | 6.9 | | | | 3.3 | 2.5 | | |
| 55 TO 59 | | | | 3.3 | 5.0 | | | | | | 2.9 | 3.2 | 3.0 | |
| 60 TO 64 | | 4.0 | 3.8 | 3.5 | 5.7 | | | | | | 1.9 | 2.7 | 2.9 | |
| 65 TO 69 | | 3.3 | 3.7 | 4.4 | 4.4 | | | | | | 2.5 | 2.7 | 3.1 | |
| | ANGLE=30° | | | | | | | | ANGLE=30° | | | | | |
| 5 TO 9 | | | | | | | | | | | | | | |
| 10 TO 14 | | 2.2 | 2.6 | | | | | | 1.3 | 2.0 | 2.2 | | | |
| 15 TO 19 | | | 3.3 | 4.4 | 4.4 | | | | | 2.4 | 2.3 | | | |
| 20 TO 24 | | | 4.0 | 5.4 | 5.9 | | | | | 3.0 | 2.6 | 2.2 | | |
| 25 TO 29 | | | | 5.2 | 5.6 | 4.3 | | | | 1.7 | 2.9 | 2.8 | | |
| 30 TO 34 | | | | 3.8 | 4.8 | | | | | | 2.4 | 2.4 | 2.4 | |
| 35 TO 39 | | | | 3.8 | 5.1 | 5.8 | | | | 2.0 | 2.5 | 2.4 | 3.6 | |
| 40 TO 44 | | | | 2.8 | 3.9 | 4.2 | 4.7 | | | | 2.6 | 2.4 | | |
| 45 TO 49 | | | | 3.8 | 4.8 | 5.3 | | | | | 2.4 | 2.6 | | |
| 50 TO 54 | | | | | 4.8 | 6.4 | 6.3 | | | | 3.0 | 2.1 | | |
| 55 TO 59 | | | | 2.9 | 4.3 | | | | | | 2.5 | 2.7 | 2.6 | |
| 60 TO 64 | | 3.8 | 3.3 | 3.1 | 4.9 | | | | | | 1.5 | 2.5 | 2.5 | |
| 65 TO 69 | | 3.0 | 3.3 | 4.1 | 3.7 | | | | | | 2.1 | 2.3 | 2.7 | |
| | ANGLE=45° | | | | | | | | ANGLE=45° | | | | | |
| 5 TO 9 | | | | | | | | | | | | | | |
| 10 TO 14 | | 1.5 | 1.9 | | | | | | 0.8 | 1.2 | 1.6 | | | |
| 15 TO 19 | | | 2.7 | 3.4 | 4.3 | | | | | 1.8 | 1.7 | | | |
| 20 TO 24 | | | 3.0 | 3.9 | 5.2 | | | | | 2.3 | 1.9 | 2.0 | | |
| 25 TO 29 | | | | 3.8 | 4.3 | 2.8 | | | | 1.2 | 2.0 | 2.2 | | |
| 30 TO 34 | | | | 2.9 | 3.8 | | | | | | 2.0 | 2.2 | 1.7 | |
| 35 TO 39 | | | | 3.0 | 3.9 | 5.6 | | | | 1.2 | 2.0 | 1.9 | 2.3 | |
| 40 TO 44 | | | | 2.7 | 3.1 | 2.9 | 3.5 | | | | 1.8 | 1.8 | | |
| 45 TO 49 | | | | 3.4 | 3.7 | 3.8 | | | | | 1.7 | 2.1 | | |
| 50 TO 54 | | | | | 3.4 | 3.7 | 4.2 | | | | 2.2 | 1.4 | | |
| 55 TO 59 | | | | 2.3 | 3.1 | | | | | | 1.8 | 2.2 | 1.9 | |
| 60 TO 64 | | 3.0 | 2.5 | 2.3 | 4.1 | | | | | | 0.8 | 1.8 | 1.7 | |
| 65 TO 69 | | 2.2 | 2.7 | 3.1 | 2.8 | | | | | | 1.5 | 1.5 | 1.9 | |
| | ANGLE=60° | | | | | | | | ANGLE=60° | | | | | |

FIG. 17

JOINT AGE WEIGHT ABDUCTION-LEFT

| AGE | JOINT AGE WEIGHT ABDUCTION-LEFT MALE-WEIGHT | | | | | | | | JOINT AGE WEIGHT ABDUCTION-LEFT FEMALE-WEIGHT | | | | | |
|---|---|---|---|---|---|---|---|---|---|---|---|---|---|---|
| | 50-99 | 100-124 | 125-149 | 150-174 | 175-199 | 200-224 | 225-249 | 250-300 | 50-99 | 100-124 | 125-149 | 150-174 | 175-199 | 200-224 |
| 5 TO 9 | | | | | | | | | | | | | | |
| 10 TO 14 | 2.3 | 2.7 | | | | | | | 1.6 | 2.4 | 2.6 | | | |
| 15 TO 19 | | | 3.4 | 4.7 | 5.5 | | | | | 2.6 | 2.4 | | | |
| 20 TO 24 | | | 3.9 | 5.0 | 6.5 | | | | | 3.2 | 2.5 | 2.3 | | |
| 25 TO 29 | | | | 5.5 | 5.7 | 8.4 | | | | 2.2 | 2.7 | 2.9 | | |
| 30 TO 34 | | | | 3.8 | 5.4 | | | | | | 2.6 | 3.0 | 2.2 | |
| 35 TO 39 | | | | 4.5 | 5.5 | 6.0 | | | | 2.3 | 2.7 | 2.9 | 3.9 | |
| 40 TO 44 | | | | 3.2 | 4.3 | 5.1 | 4.3 | | | | 2.2 | 2.6 | | |
| 45 TO 49 | | | | 4.5 | 4.7 | 5.5 | | | | | 2.6 | 2.6 | | |
| 50 TO 54 | | | | | 4.6 | 5.8 | 6.0 | | | | 1.9 | 2.2 | | |
| 55 TO 59 | | | | 3.3 | 4.0 | | | | | | 2.3 | 2.7 | 3.0 | |
| 60 TO 64 | | | 3.5 | 3.3 | 3.0 | 5.0 | | | | | 1.7 | 2.3 | 2.5 | |
| 65 TO 69 | | | 3.0 | 3.2 | 3.5 | 4.1 | | | | | 1.9 | 2.3 | 3.0 | |
| | ANGLE=30° | | | | | | | | ANGLE=30° | | | | | |
| 5 TO 9 | | | | | | | | | | | | | | |
| 10 TO 14 | 2.0 | 2.1 | | | | | | | 1.3 | 2.0 | 2.5 | | | |
| 15 TO 19 | | | 2.5 | 4.2 | 4.3 | | | | | 2.5 | 2.0 | | | |
| 20 TO 24 | | | 3.4 | 4.3 | 4.6 | | | | | 2.2 | 2.2 | 1.7 | | |
| 25 TO 29 | | | | 4.9 | 5.1 | 5.4 | | | | 1.7 | 2.6 | 2.6 | | |
| 30 TO 34 | | | | 3.1 | 4.5 | | | | | | 2.4 | 2.7 | 2.0 | |
| 35 TO 39 | | | | 3.9 | 4.8 | 5.4 | | | | 2.0 | 2.5 | 2.0 | 3.2 | |
| 40 TO 44 | | | | 2.7 | 3.5 | 4.2 | 4.0 | | | | 1.8 | 1.9 | | |
| 45 TO 49 | | | | 3.2 | 4.0 | 4.7 | | | | | 2.2 | 2.3 | | |
| 50 TO 54 | | | | | 4.1 | 4.8 | 5.5 | | | | 2.0 | 2.0 | | |
| 55 TO 59 | | | | 2.8 | 3.8 | | | | | | 2.0 | 2.3 | 2.6 | |
| 60 TO 64 | | | 3.1 | 3.0 | 2.4 | 4.4 | | | | | 1.2 | 2.0 | 2.0 | |
| 65 TO 69 | | | 2.6 | 2.8 | 3.0 | 3.4 | | | | | 1.5 | 2.0 | 2.5 | |
| | ANGLE=45° | | | | | | | | ANGLE=45° | | | | | |
| 5 TO 9 | | | | | | | | | | | | | | |
| 10 TO 14 | 1.4 | 1.6 | | | | | | | 0.9 | 1.2 | 1.6 | | | |
| 15 TO 19 | | | 2.3 | 3.2 | 3.5 | | | | | 2.0 | 1.5 | | | |
| 20 TO 24 | | | 2.9 | 3.3 | 3.7 | | | | | 1.8 | 1.5 | 1.2 | | |
| 25 TO 29 | | | | 3.6 | 4.2 | 3.2 | | | | 1.1 | 1.9 | 1.9 | | |
| 30 TO 34 | | | | 2.6 | 3.9 | | | | | | 1.7 | 1.8 | 1.7 | |
| 35 TO 39 | | | | 2.7 | 3.5 | 4.8 | | | | 1.2 | 1.8 | 1.4 | 2.7 | |
| 40 TO 44 | | | | 2.0 | 2.9 | 3.1 | 3.1 | | | | 1.2 | 1.6 | | |
| 45 TO 49 | | | | 3.2 | 2.8 | 3.5 | | | | | 1.6 | 1.7 | | |
| 50 TO 54 | | | | | 3.0 | 3.8 | 4.4 | | | | 1.5 | 1.5 | | |
| 55 TO 59 | | | | 2.0 | 2.9 | | | | | | 1.5 | 1.5 | 1.9 | |
| 60 TO 64 | | | 2.8 | 2.3 | 1.8 | 3.5 | | | | | 0.8 | 1.5 | 1.5 | |
| 65 TO 69 | | | 1.7 | 2.2 | 2.1 | 2.7 | | | | | 1.2 | 1.4 | 1.9 | |
| | ANGLE=60° | | | | | | | | ANGLE=60° | | | | | |

FIG. 18

JOINT AGE WEIGHT ADDUCTION-RIGHT

| AGE | JOINT AGE WEIGHT ADDUCTION-RIGHT MALE-WEIGHT | | | | | | | JOINT AGE WEIGHT ADDUCTION-RIGHT FEMALE-WEIGHT | | | | | |
|---|---|---|---|---|---|---|---|---|---|---|---|---|---|
| | 50-99 | 100-124 | 125-149 | 150-174 | 175-199 | 200-224 | 225-249 | 250-300 | 50-99 | 100-124 | 125-149 | 150-174 | 175-199 | 200-224 |
| 5 TO 9 | | | | | | | | | | | | | | |
| 10 TO 14 | | 11.8 | 12.8 | | | | | | 10.9 | 10.7 | 11.9 | | | |
| 15 TO 19 | | | 14.3 | 16.2 | 16.4 | | | | | 11.0 | 13.5 | | | |
| 20 TO 24 | | | 15.2 | 17.4 | 18.5 | | | | | | 13.2 | 14.4 | 14.0 | |
| 25 TO 29 | | | | 17.8 | 19.7 | 20.8 | | | | | 10.8 | 15.2 | 16.0 | |
| 30 TO 34 | | | | 17.4 | 17.4 | | | | | | | 12.9 | 16.4 | 16.2 |
| 35 TO 39 | | | | 18.5 | 16.9 | 19.2 | | | | | 12.0 | 14.1 | 14.4 | 12.2 |
| 40 TO 44 | | | | 17.1 | 16.0 | 20.9 | 18.0 | | | | | 13.7 | 12.9 | |
| 45 TO 49 | | | | 15.3 | 17.1 | 18.2 | | | | | | 12.0 | 14.8 | |
| 50 TO 54 | | | | | 16.5 | 17.3 | 15.6 | | | | | 13.1 | 13.8 | |
| 55 TO 59 | | | | 14.3 | 16.1 | | | | | | | 13.5 | 16.2 | 15.6 |
| 60 TO 64 | | | 12.9 | 13.8 | 12.4 | 16.3 | | | | | | 12.0 | 13.0 | 13.3 |
| 65 TO 69 | | | 12.6 | 13.4 | 15.5 | 13.1 | | | | | | 11.0 | 12.3 | 14.1 |
| | ANGLE=30° | | | | | | | | ANGLE=30° | | | | | |
| 5 TO 9 | | | | | | | | | | | | | | |
| 10 TO 14 | | 11.9 | 13.3 | | | | | | 11.9 | 11.3 | 12.8 | | | |
| 15 TO 19 | | | 15.9 | 18.0 | 18.6 | | | | | 12.7 | 15.0 | | | |
| 20 TO 24 | | | 18.0 | 18.4 | 20.7 | | | | | | 14.9 | 15.1 | 15.2 | |
| 25 TO 29 | | | | 19.1 | 21.3 | 20.9 | | | | | 11.6 | 16.6 | 17.8 | |
| 30 TO 34 | | | | 19.4 | 18.8 | | | | | | | 14.2 | 17.4 | 17.2 |
| 35 TO 39 | | | | 20.7 | 18.4 | 19.2 | | | | | 12.6 | 14.9 | 15.7 | 15.4 |
| 40 TO 44 | | | | 17.5 | 16.2 | 19.9 | 20.4 | | | | | 14.5 | 13.7 | |
| 45 TO 49 | | | | 16.9 | 19.1 | 19.4 | | | | | | 13.4 | 16.1 | |
| 50 TO 54 | | | | | 18.2 | 18.9 | 16.9 | | | | | 15.7 | 15.1 | |
| 55 TO 59 | | | | 14.6 | 17.5 | | | | | | | 15.1 | 16.9 | 17.5 |
| 60 TO 64 | | | 12.4 | 15.6 | 13.6 | 17.1 | | | | | | 11.9 | 14.9 | 14.7 |
| 65 TO 69 | | | 13.5 | 14.6 | 16.5 | 15.4 | | | | | | 12.7 | 12.8 | 15.1 |
| | ANGLE=45° | | | | | | | | ANGLE=45° | | | | | |
| 5 TO 9 | | | | | | | | | | | | | | |
| 10 TO 14 | | 13.2 | 14.2 | | | | | | 12.5 | 13.2 | 14.2 | | | |
| 15 TO 19 | | | 17.5 | 19.3 | 19.1 | | | | | 13.4 | 16.0 | | | |
| 20 TO 24 | | | 20.3 | 20.5 | 21.7 | | | | | | 15.8 | 16.7 | 14.9 | |
| 25 TO 29 | | | | 21.2 | 22.2 | 22.1 | | | | | 12.3 | 18.4 | 18.9 | |
| 30 TO 34 | | | | 20.3 | 20.9 | | | | | | | 15.0 | 19.3 | 15.7 |
| 35 TO 39 | | | | 21.8 | 20.3 | 20.3 | | | | | 14.1 | 17.1 | 17.1 | 14.4 |
| 40 TO 44 | | | | 20.7 | 18.1 | 22.1 | 21.2 | | | | | 16.8 | 14.6 | |
| 45 TO 49 | | | | 18.5 | 20.5 | 21.1 | 19.0 | | | | | 14.4 | 16.4 | |
| 50 TO 54 | | | | | 20.3 | 21.1 | | | | | | 15.5 | 15.8 | |
| 55 TO 59 | | | | 15.4 | 18.8 | | | | | | | 15.7 | 17.6 | 17.9 |
| 60 TO 64 | | | 14.2 | 16.1 | 15.2 | 19.1 | | | | | | 12.7 | 15.6 | 15.8 |
| 65 TO 69 | | | 14.8 | 15.8 | 17.6 | 16.4 | | | | | | 13.2 | 14.3 | 16.0 |
| | ANGLE=60° | | | | | | | | ANGLE=60° | | | | | |

FIG. 19

JOINT AGE WEIGHT ADDUCTION-LEFT

| AGE | JOINT AGE WEIGHT ADDUCTION-LEFT MALE-WEIGHT | | | | | | | JOINT AGE WEIGHT ADDUCTION-LEFT FEMALE-WEIGHT | | | | | |
|---|---|---|---|---|---|---|---|---|---|---|---|---|---|
| | 50-99 | 100-124 | 125-149 | 150-174 | 175-199 | 200-224 | 225-249 | 250-300 | 50-99 | 100-124 | 125-149 | 150-174 | 175-199 | 200-224 |
| 5 TO 9 | | | | | | | | | | | | | | |
| 10 TO 14 | | 10.8 | 12.5 | | | | | | 10.1 | 10.2 | 12.4 | | | |
| 15 TO 19 | | | 13.9 | 16.3 | 19.0 | | | | | 11.5 | 12.4 | | | |
| 20 TO 24 | | | 15.0 | 16.7 | 17.0 | | | | | 12.7 | 13.4 | 12.7 | | |
| 25 TO 29 | | | | 17.2 | 18.9 | 14.4 | | | | 12.1 | 13.9 | 14.6 | | |
| 30 TO 34 | | | | 17.3 | 16.8 | | | | | | 12.1 | 15.6 | 16.0 | |
| 35 TO 39 | | | | 19.5 | 16.5 | 17.8 | | | | 12.2 | 13.2 | 14.4 | 13.2 | |
| 40 TO 44 | | | | 14.5 | 15.7 | 18.9 | 17.9 | | | | 12.3 | 12.2 | | |
| 45 TO 49 | | | | 15.6 | 17.3 | 17.9 | | | | | 10.5 | 14.0 | | |
| 50 TO 54 | | | | | 17.2 | 16.3 | 15.3 | | | | 12.7 | 12.7 | | |
| 55 TO 59 | | | | 12.4 | 15.4 | | | | | | 13.1 | 14.4 | 13.5 | |
| 60 TO 64 | | | 11.5 | 13.5 | 11.6 | 16.2 | | | | | 11.1 | 12.7 | 12.8 | |
| 65 TO 69 | | | 12.9 | 13.3 | 14.3 | 14.7 | | | | | 11.0 | 11.8 | 12.9 | |
| | ANGLE=30° | | | | | | | | ANGLE=30° | | | | | |
| 5 TO 9 | | | | | | | | | | | | | | |
| 10 TO 14 | | 12.1 | 13.4 | | | | | | 11.3 | 10.2 | 12.9 | | | |
| 15 TO 19 | | | 15.8 | 18.1 | 20.9 | | | | | 10.8 | 13.4 | | | |
| 20 TO 24 | | | 16.3 | 18.3 | 19.8 | | | | | 13.7 | 14.4 | 14.1 | | |
| 25 TO 29 | | | | 18.7 | 21.0 | 20.6 | | | | 11.9 | 15.2 | 17.2 | | |
| 30 TO 34 | | | | 17.0 | 18.1 | | | | | | 13.8 | 16.9 | 18.4 | |
| 35 TO 39 | | | | 20.7 | 18.8 | 18.2 | | | | 12.0 | 14.6 | 16.5 | 13.7 | |
| 40 TO 44 | | | | 14.2 | 15.8 | 18.5 | 17.8 | | | | 12.5 | 12.1 | | |
| 45 TO 49 | | | | 15.7 | 17.8 | 18.3 | | | | | 11.1 | 15.1 | | |
| 50 TO 54 | | | | | 18.5 | 17.3 | 16.6 | | | | 15.1 | 13.5 | | |
| 55 TO 59 | | | | 13.6 | 17.6 | | | | | | 14.7 | 14.5 | 15.8 | |
| 60 TO 64 | | | 11.2 | 15.1 | 13.2 | 16.5 | | | | | 12.1 | 13.9 | 15.1 | |
| 65 TO 69 | | | 13.3 | 14.4 | 16.0 | 16.8 | | | | | 12.6 | 13.2 | 14.3 | |
| | ANGLE=45° | | | | | | | | ANGLE=45° | | | | | |
| 5 TO 9 | | | | | | | | | | | | | | |
| 10 TO 14 | | 12.4 | 14.5 | | | | | | 11.6 | 10.8 | 13.8 | | | |
| 15 TO 19 | | | 17.1 | 19.2 | 20.3 | | | | | 11.6 | 15.4 | | | |
| 20 TO 24 | | | 17.7 | 20.7 | 20.9 | | | | | 14.7 | 15.7 | 14.9 | | |
| 25 TO 29 | | | | 20.1 | 22.3 | 21.8 | | | | 11.8 | 16.5 | 18.3 | | |
| 30 TO 34 | | | | 18.6 | 19.7 | | | | | | 13.9 | 18.4 | 16.8 | |
| 35 TO 39 | | | | 21.3 | 20.2 | 20.3 | | | | 12.8 | 15.2 | 15.7 | 14.3 | |
| 40 TO 44 | | | | 16.1 | 17.3 | 21.0 | 19.0 | | | | 13.6 | 13.2 | | |
| 45 TO 49 | | | | 17.4 | 20.2 | 20.9 | | | | | 12.8 | 16.3 | | |
| 50 TO 54 | | | | | 20.1 | 20.1 | 18.4 | | | | 16.0 | 14.6 | | |
| 55 TO 59 | | | | 15.3 | 19.2 | | | | | | 16.0 | 16.4 | 18.7 | |
| 60 TO 64 | | | 11.4 | 15.6 | 14.4 | 18.7 | | | | | 13.3 | 15.8 | 16.5 | |
| 65 TO 69 | | | 14.2 | 15.1 | 17.9 | 17.2 | | | | | 13.6 | 14.4 | 15.0 | |
| | ANGLE=60° | | | | | | | | ANGLE=60° | | | | | |

FIG. 20

GRIP STRENGTH BY AGE AND WEIGHT FOR MALE AND FEMALE LEFT AND RIGHT

MALE   LEFT/RIGHT GRIP

| WEIGHT / AGE | 50 TO 99 | 100 TO 124 | 125 TO 149 | 150 TO 174 | 175 TO 199 | 200 TO 224 | 225 TO 249 | 250 TO 300 |
|---|---|---|---|---|---|---|---|---|
| 10 TO 14 |  | 59/66 |  |  |  |  |  |  |
| 15 TO 19 |  |  | 68/70 |  |  |  |  |  |
| 20 TO 24 |  |  | 93/97 | 101/104 | 110/120 |  |  |  |
| 25 TO 29 |  |  | 94/110 | 118/125 | 130/137 |  |  |  |
| 30 TO 34 |  |  |  | 114/117 | 128/132 |  |  |  |
| 35 TO 39 |  |  | 80/91 | 105/108 | 120/126 |  |  |  |
| 40 TO 44 |  |  |  | 110/114 | 117/126 | 129/137 |  |  |
| 45 TO 49 |  |  |  | 94/96 | 105/108 | 126/136 |  |  |
| 50 TO 54 |  |  |  | 97/98 | 96/103 | 128/139 | 111/119 |  |
| 55 TO 59 |  |  |  |  | 97/100 | 119/125 |  |  |
| 60 TO 64 |  |  | 70/82 | 74/82 | 98/101 | 106/110 | 105/113 |  |
| 65 TO 69 |  |  | 73/78 | 81/86 | 77/83 | 95/102 |  |  |
|  |  |  |  | 74/81 | 89/92 | 84/84 |  |  |

FEMALE   LEFT/RIGHT GRIP

| WEIGHT / AGE | 50 TO 99 | 100 TO 124 | 125 TO 149 | 150 TO 174 | 175 TO 199 | 200 TO 224 | 225 TO 249 | 250 TO 300 |
|---|---|---|---|---|---|---|---|---|
| 10 TO 14 | 56/56 | 63/59 | 74/70 | 82/82 |  |  |  |  |
| 15 TO 19 |  | 66/60 | 77/71 | 80/74 |  |  |  |  |
| 20 TO 24 |  | 84/78 | 78/71 | 83/77 |  |  |  |  |
| 25 TO 29 |  | 58/51 | 81/74 | 81/84 | 79/75 |  |  |  |
| 30 TO 34 |  |  | 72/64 | 80/73 | 81/80 |  |  |  |
| 35 TO 39 |  | 66/61 | 79/72 | 71/69 |  |  |  |  |
| 40 TO 44 |  |  | 65/62 | 75/72 |  |  |  |  |
| 45 TO 49 |  |  | 68/64 | 65/61 |  |  |  |  |
| 50 TO 54 |  |  | 66/65 | 72/70 | 77/73 |  |  |  |
| 55 TO 59 |  |  | 69/64 | 70/68 | 71/66 |  |  |  |
| 60 TO 64 |  |  | 58/54 | 69/65 | 75/69 |  |  |  |
| 65 TO 69 |  |  | 66/59 |  |  |  |  |  |

FIG. 21

CORRELATION COEFFICIENTS FOR ALL SUBJECTS
MALES

| VARIABLES | AGE | WEIGHT | R-GRIP | L-GRIP | ABR30 | ABR45 | ABR60 | ADR30 | ADR45 | ADR60 | ABL30 | ABL45 | ABL60 | ADL30 | ADL45 | ADL60 |
|---|---|---|---|---|---|---|---|---|---|---|---|---|---|---|---|---|
| AGE | | 0.41 | -0.16 | -0.16 | -0.01 | 0.01 | -0.02 | -0.11 | -0.08 | -0.08 | -0.07 | -0.02 | -0.03 | -0.07 | -0.11 | -0.08 |
| WEIGHT | | | 0.46 | 0.48 | 0.5 | 0.46 | 0.46 | 0.35 | 0.35 | 0.35 | 0.5 | 0.46 | 0.42 | 0.33 | 0.33 | 0.38 |
| R-GRIP | | | | | 0.75 | 0.67 | 0.64 | 0.74 | 0.73 | 0.75 | 0.73 | 0.64 | 0.59 | 0.65 | 0.65 | 0.68 |
| L-GRIP | | | | | 0.77 | 0.69 | 0.64 | 0.73 | 0.72 | 0.74 | 0.77 | 0.69 | 0.64 | 0.68 | 0.68 | 0.71 |
| ABR30 | | | | | | 0.83 | 0.85 | 0.62 | 0.63 | 0.65 | 0.84 | 0.83 | 0.8 | 0.57 | 0.55 | 0.61 |
| ABR45 | | | | | | | 0.87 | 0.55 | 0.57 | 0.6 | 0.78 | 0.81 | 0.77 | 0.52 | 0.5 | 0.56 |
| ABR60 | | | | | | | | 0.52 | 0.55 | 0.56 | 0.73 | 0.75 | 0.78 | 0.55 | 0.5 | 0.52 |
| ADR30 | | | | | | | | | 0.86 | | 0.6 | 0.56 | 0.5 | 0.77 | 0.73 | 0.74 |
| ADR45 | | | | | | | | | | 0.88 | 0.57 | 0.56 | 0.51 | 0.79 | 0.8 | 0.82 |
| ADR60 | | | | | | | | | | | 0.6 | 0.59 | 0.53 | 0.79 | 0.79 | 0.83 |
| ABL30 | | | | | | | | | | | | 0.88 | 0.81 | 0.57 | 0.61 | 0.6 |
| ABL45 | | | | | | | | | | | | | 0.87 | 0.55 | 0.55 | 0.57 |
| ABL60 | | | | | | | | | | | | | | 0.51 | 0.49 | 0.5 |
| ADL30 | | | | | | | | | | | | | | | 0.86 | 0.82 |
| ADL45 | | | | | | | | | | | | | | | | 0.88 |

FEMALES

| VARIABLES | AGE | WEIGHT | R-GRIP | L-GRIP | ABR30 | ABR45 | ABR60 | ADR30 | ADR45 | ADR60 | ABL30 | ABL45 | ABL60 | ADL30 | ADL45 | ADL60 |
|---|---|---|---|---|---|---|---|---|---|---|---|---|---|---|---|---|
| AGE | | 0.52 | -0.04 | -0.01 | 0.01 | 0.07 | 0 | 0.07 | 0.08 | 0.07 | 0.03 | 0.01 | 0.02 | 0.06 | 0.13 | 0.19 |
| WEIGHT | | | 0.35 | 0.37 | 0.23 | 0.26 | 0.2 | 0.28 | 0.32 | 0.29 | 0.21 | 0.17 | 0.22 | 0.26 | 0.33 | 0.31 |
| R-GRIP | | | | 0.87 | 0.58 | 0.55 | 0.51 | 0.56 | 0.62 | 0.62 | 0.42 | 0.4 | 0.39 | 0.49 | 0.52 | 0.55 |
| L-GRIP | | | | | 0.49 | 0.45 | 0.41 | 0.53 | 0.58 | 0.57 | 0.49 | 0.46 | 0.41 | 0.56 | 0.58 | 0.58 |
| ABR30 | | | | | | 0.83 | 0.73 | 0.41 | 0.42 | 0.48 | 0.67 | 0.58 | 0.56 | 0.37 | 0.35 | 0.38 |
| ABR45 | | | | | | | 0.81 | 0.35 | 0.38 | 0.43 | 0.56 | 0.56 | 0.57 | 0.31 | 0.31 | 0.34 |
| ABR60 | | | | | | | | 0.32 | 0.32 | 0.36 | 0.51 | 0.51 | 0.57 | 0.3 | 0.31 | 0.34 |
| ADR30 | | | | | | | | | 0.88 | 0.85 | 0.32 | 0.3 | 0.23 | 0.79 | 0.74 | 0.71 |
| ADR45 | | | | | | | | | | 0.88 | 0.3 | 0.31 | 0.26 | 0.74 | 0.75 | 0.74 |
| ADR60 | | | | | | | | | | | 0.36 | 0.35 | 0.26 | 0.72 | 0.72 | 0.74 |
| ABL30 | | | | | | | | | | | | 0.82 | 0.63 | 0.4 | 0.4 | 0.4 |
| ABL45 | | | | | | | | | | | | | 0.77 | 0.39 | 0.38 | 0.41 |
| ABL60 | | | | | | | | | | | | | | 0.3 | 0.29 | 0.31 |
| ADL30 | | | | | | | | | | | | | | | 0.88 | 0.8 |
| ADL45 | | | | | | | | | | | | | | | | 0.88 |

FIG. 31

SYSTEM AND METHOD FOR MEASURING THE MOTOR STRENGTH OF A HUMAN THUMB OR FINGER

RELATED APPLICATION

This application claims priority from U.S. Provisional Application No. 60/428,277, filed on Nov. 22, 2002, which is incorporated herein by reference.

BACKGROUND OF THE INVENTION

1. Field of the Invention

The present invention generally relates to a system and method for measuring the motor strength of a human thumb or finger.

2. Background of the Invention

Despite great technological advancements in the field of hand surgery over the past twenty-five years, grip and pinch strength are the only two ways to quantitatively measure motor strength in the hand. A grip meter can be used to assess these parameters to make assessments as to focal areas of strength and weakness in the hand that may be due to primary muscle pathology, nerve and motor end-plate disease, and/or disorders of bone and joint. Variations in pinch such as tip, chuck, or key pinch are commonly used to mimic various activities of daily living. The Medico-Legal Society and workers compensation communities, as part of disability and return to work assessments, extensively use hand surgery research, daily clinical practice and the data obtained from grip and strength measurements.

The limitation of grip and pinch tests I have determined lies in the fact that both of these testing modalities evaluate muscle groups that are innervated jointly by the median and ulnar nerves. Grip strength is a composite function with contributions from all the palmar digits, as well as synergistic firing of intrinsic and extrinsic digital flexors. The extrinsic flexors of the sublimis and profundus groups of the hand are dually innervated in the forearm, whereas the intrinsic flexors are primarily ulnarly innervated, and the radial two lumbricals are median innervated.

With pinch strength, the same issues exist. The abductor policies brevis is served almost entirely by the median nerve. The adductor pollicis and the first dorsal interosseous are nearly completely ulnarly innervated. The remaining muscles, the flexor pollicis brevis and the opponens pollicis, show wide variations in median and ulnar innervations.

A quantitative measure of forces generated in pure palmar thumb adduction and abduction, I have determined, could serve as an adjunct to grip and pinch strength in the following conditions:

osteo-arthritis pre-operation and post-operation;
rheumatoid arthritis pre-operation and post-operation;
thumb reconstruction after trauma;
reconstruction of congenital differences;
following tendon transfer surgery; and/or
following tumor resection and reconstruction.

Instruments that evaluate the function of the human hand can be divided into three general types. First, instruments that measure the motor strength of the thumb and fingers in various positions of pinch and grip. Second, sensory measuring devices that assess fine touch, sharp-dull, two-point discrimination, pressure and temperature sensation. Third, dexterity measuring devices that assess neuromuscular coordination such as pegboard or Moberg instruments.

While existing pinch strength devices assess global functioning of the intrinsic thumb muscles, there is no known instrument that significantly, substantially and/or completely isolates one or more muscles that are enervated by the motor branch of the median nerve. As the motor branch enters the thenar eminence, I have determined that it enervates the abductor pollicis brevis, the opponens pollicis, and the superficial head of the flexor pollicis brevis. Other muscles are powered by the terminal motor branches of the ulnar nerve. These muscles are the deep head of the flexor pollicis brevis, the adductor pollicis, the first dorsal interosseous, and some fibers of the opponens pollicis. The simple act of pinch is actually a complex interplay of all the above muscles, and therefore there is no way to independently assess the function of those muscles that are enervated by the median nerve alone.

Muscles that abduct, or bring the thumb out of the palm in a vector perpendicular to the palm, are innervated by the median nerve. Muscles that adduct, or bring the thumb back toward the palm, are innervated by the ulnar nerve. There is no known device that can measure the force generated by these muscles.

For example, one known apparatus for exercising the human hand is described in PCT Publication WO/018018A2, which is incorporated herein by reference. As shown in the schematic illustration of FIG. 1, the assembly 110 includes two major components, a tension member 112 and a compression member 114. The compression member 114 is formed of a resiliently compressible material, such as open cell polyurethane foam, and in the embodiment that is illustrated, is configured as a generally spherical ball 116.

The tension member 112 is configured as an elongate, unitary tether 118 formed of a suitable elastomeric material, such as flexible PVC or latex rubber, for example. The tether 118 includes a main cord 120 that extends through a bore 122 in the compressible ball 116. A thumb loop 124 is mounted on the lower end of the main cord so as to project from the bottom of the compressible member, and a stabilizing web 126 is formed on the upper end of the cord. The stabilizing web protrudes slightly above the upper end of the ball, and finger loops 130, 132, 134 and 136 are attached to the web by comparatively short, narrow elastic cords 140, 142, 144 and 146. The finger cords 140–146 extend from the stabilizing web at predetermined angles so as to develop the correct force vectors for property exercising the hand.

The thumb loop and the finger loops are sized to fit over the middle phalanges of their respective digits, and are also provided with outwardly projecting tab portions 148 which aid in placing the loops by providing a grip for the fingers of the opposite hand.

Tapered junctions 150, 152 are preferably formed where the web and the thumb loop join the main cord. In addition to providing added strength and resistance to tearing in these areas, the tapered junctions 150, 152 engage corresponding recesses 154a, 154b at the ends of the bore 122 through the compressible ball member, thereby providing a firmer, more stable fit between the two members.

Thus, when the exercise assembly is installed on a user's hand, the fingers and thumb are able to move through their full ranges of motion, with the tension member offering a predetermined degree of resistance in the extension-abduction or adduction direction and the compression member providing a predetermined degree of resistance in the flexion-adduction-opposition direction. Moreover, the resistance is apportioned properly amongst the fingers of the hand, and the confirmation of the assembly ensures that the muscles and tendons are exercised together in a coordinated fashion. In addition, the configuration of the compressible ball and the tether structure enable the assembly 110 to be used with either hand, by simply reversing the assembly and installing the cords on the corresponding fingers of the other hand.

Therefore, the apparatus shown in FIG. 1 in no way quantitatively measures the forces generated by the thumb in abduction and adduction.

SUMMARY OF THE INVENTION

One embodiment of the present invention provides a system for measuring muscle strength of a human thumb. The system includes a first structure, optionally moveable, that contacts at least a portion of a back side of the hand, and a second structure, optionally in a substantially fixed position, that contacts at least a portion of a palm of the hand. The first and second structures configured to secure the hand in a substantially fixed position. A ring is provided that receives a thumb, and a load cell includes electronics to record a force generated by the thumb. A mechanical assembly is also provided that links the ring and the load cell to transmit the forces from the ring to the load cell.

The mechanical assembly may include a threaded shaft and a nut, with the ring configured to transmit the force generated by the thumb to the threaded shaft and the nut. The mechanical assembly can further include a beam positioned substantially perpendicular to the threaded shaft, with the beam transmitting the load from the threaded shaft to the load cell. The system may also include a knob for rotating the threaded shaft to adjust the position of the nut on the threaded shaft.

In addition, the system may include a push plate, at least one push rod that contacts the push plate and the first structure, a bolt secured to the first structure, and a handle threaded to negotiate the bolt, wherein upon rotating the handle in a first direction, the push plate, the at least one push rod and the second structure move in a direction to adjustably secure the hand in the substantially foxed position.

The electronics provides the capability to at least one of: a) display and record forces in at least one of metric end English units; b) display and record a peak force; c) continuously display and record forces generated by the thumb; and d) reset the system prior to a next exertion of force by the thumb. A connection may also be provided that transmits the data recorded by the system to a computing device.

In another embodiment, the system can include a first plate that contacts at least a portion of a back side of the hand, and a second plate that contacts at least a portion of a palm of the hand. The first and second plates are configured to secure the hand in a substantially fixed position. A ring is provided to receive a thumb of the hand, and a load cell that includes electronics records a force generated by the thumb. A mechanical assembly links the ring and the load cell to transmit the force from the ring to the load cell.

In another embodiment, a system for measuring muscle strength of a human thumb includes a clamping apparatus to secure a hand in a substantially fixed position, a structure for receiving a thumb of the hand while the hand is in the substantially fixed position, a force measuring device to record a force generated by the thumb in at least one of abduction and adduction directions, and a mechanical assembly that transmits the force generated by the thumb to the force measuring device. The force measuring device optionally continuously records forces generated by the thumb over a finite period of time. The structure is optionally adjustable with respect to the hand when the hand is in the substantially fixed position.

In another embodiment, a system for measuring muscle strength of a thumb or a finger of a hand is provided that includes a securing apparatus to secure a hand in a substantially fixed position, a structure that is connected to the securing apparatus to receive the thumb or finger of the hand while the hand is in the substantially fixed position, and a force measuring and recording device, responsively connected to the structure, to measure at least one force generated by the thumb or finger in the structure in at least one of abduction and adduction directions, and record the at least one force to be used in at least one of diagnostic and therapeutic treatment of the thumb or finger.

A quantitative measure of forces generated in pure palmar thumb adduction and abduction may serve as an adjunct to grip and pinch strength in the following conditions: a) osteo-arthritis pre-operation and post-operation; b) rheumatoid arthritis pre-operation and post-operation; c) thumb reconstruction after trauma; d) reconstruction of congenital differences; d) following tendon transfer surgery; and/or e) following tumor resection and reconstruction. In addition, the system significantly, substantially and/or completely isolates one or more muscles that are enervated by the motor branch of the median nerve.

A method for measuring muscle strength of a human thumb in accordance with the present invention includes securing a hand in a substantially fixed position, placing a thumb of the hand in a structure that enables the thumb to generate a measurable force in at least one of the abduction and adduction directions, and recording the force. The method optionally includes providing electronics to record the force generated by the thumb, and providing a mechanical assembly linking the structure to the electronics to transmit the force from the structure to the electronics.

The thumb can move in at least a first direction and a substantially opposing second direction. In addition, the method optionally includes adjusting at least a portion of the structure with respect to the hand.

Further, forces may be displayed in at least one of metric end English units. A peak force generated by the thumb may be displayed, forces generated by the thumb or may be continuously displayed. Recorded forces may be transmitted from the system to a second system.

Another method to measure muscle strength of a thumb or a finger of a hand in accordance with the invention includes at least one of the sequential, non-sequential and sequence independent steps of securing the hand in a substantially fixed position, receiving the thumb or the finger of the hand in a force measuring device, measuring the force generated by the thumb or the finger in at least one of the abduction and adduction directions, and transmitting the force generated by the thumb or the finger to be used in at least one of diagnostic and therapeutic treatment of the thumb or finger. One or more muscles that are enervated by the motor branch of the median nerve are significantly, substantially and/or completely isolated.

Embodiments of the apparatus in accordance with the present invention can thus quantitatively measure, for example, the power of palmar adduction and abduction of the thumb, reflecting the function of median and ulnarly innervated neuro-muscular units separately, thus providing specific information of their integrity.

Embodiments of an apparatus in accordance with the present invention can be used, for example, to measure a degree of motor function in the median nerve in carpal tunnel syndrome and/or the ulnar nerve in ulnar neuropathy, optionally as a preoperative assessment and/or post operative follow up. Patients recovering from injuries to the median nerve and ulnar nerve, and those who have undergone opponensplasty, can be assessed.

In addition, embodiments of the present invention can be used to test neurological conditions, such as cerebral palsy, stroke victims, and motor wasting conditions such as Charcot-Marie-Tooth, which affect the intrinsic muscles of the hand. The ability to abduct and adduct the thumb is affected by basal joint arthritis, and the difference between pre- and post-operative abductor and adductor strength can be one indicator of success. Embodiments of the invention can also include an isokinetic mode that allows controlled motion with varying loads that can assist in muscle conditioning of the thumb.

In view of the foregoing, it should be apparent that embodiments of the present invention can advantageously be used, for example, in the following clinical specialties:

Orthopaedic and Plastic Hand Surgeons;
Orthopaedic Surgeons;
Physical Medicine and Rehabilitation Medicine Physicians;
Physical and Occupational Therapists;
Neurologists;
Rheumatologists;
Family Practice Physicians;
Osteopaths; and/or
Chiropractors.

There has thus been outlined, rather broadly, the features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention. Other features of the present invention will be evident to those of ordinary skill, particularly upon consideration of the following detailed description of the preferred embodiments.

BRIEF DESCRIPTION OF THE DRAWINGS

The detailed description of the present application showing various distinctive features may be best understood when the detailed description is read in reference to the appended drawing in which:

FIG. 7A is a top sectional view of the ring plate.

FIG. 7B is an elevation view of the ring plate.

FIG. 16 is a data table showing age, weight and sex characteristics for right dominant subjects.

FIG. 17 is a data table showing abduction strength for right dominant males and females by joint age and weight.

FIG. 18 is a data table showing abduction strength for left dominant males and females by joint age and weight.

FIG. 19 is a data table showing adduction strength for right dominant males and females by joint age and weight.

FIG. 20 is a data table showing adduction strength for left dominant males and females by joint age and weight.

FIG. 21 is a data table showing grip strength by age and weight for both left and right dominant males and females.

FIG. 31 is a data table showing correlation coefficients for all subjects by sex, age and weight at 30, 45 and 60 degree positions.

DETAILED DESCRIPTION OF THE INVENTION

Figure 1:
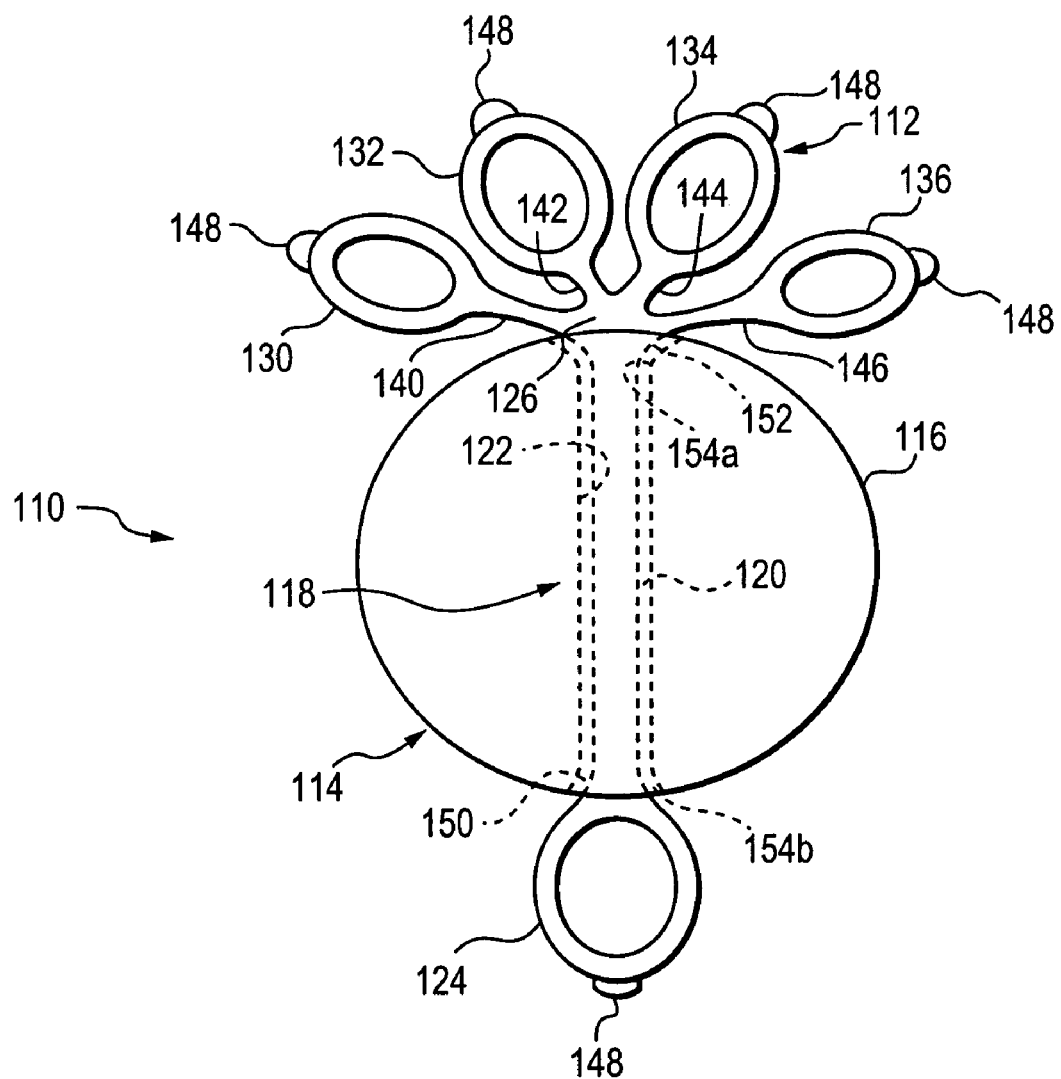
FIGS. 1 is a diagram illustrating a conventional apparatus for exercising the human hand.

Reference now will be made in detail to the presently preferred embodiments of the invention. Such embodiments are provided by way of explanation of the invention, which is not intended to be limited thereto. In fact, those of ordinary skill in the art may appreciate upon reading the present specification and viewing the present drawings that various modifications and variations can be made.

For example, features illustrated or described as part of one embodiment can be used on other embodiments to yield a still further embodiment. Additionally, certain features may be interchanged with similar devices or features not mentioned yet which perform the same or similar functions. It is therefore intended that such modifications and variations are included within the totality of the present invention.

As illustrated, for example, in FIGS. 2–8, embodiments of the present invention are directed to an apparatus 200 for measuring forces generated by a human thumb. A base 202 is shown, having a bottom plate 204, a top plate 206, and sides. Top plate 206 and bottom plate 204 are secured to base 202 by any suitable known securing means, such as bolts 232, which are located at each corner of base 202. Base 202 includes a display 210 for displaying measured thumb forces, and switches 208a–f, as shown in FIGS. 2A and 2B. Switch 208a can be used to display the force exerted by the thumb on display 202, on a display (not shown) on an opposing side of base 202, or both displays. Switch 208b can be used to select force measurement in either pounds or kilograms. Switch 208c can be used to select to display a peak or maximum force, or a continuously updated display of measured force. Switch 208d can be used to zero out the forces between recordings. Switch 208e is used to turn the apparatus on and off. Finally, switch 208f can be used to select either abduction (i.e., movement away from the palm of the hand) or adduction (i.e., movement toward the palm of the hand) movement of the thumb.

Vertical housing 214 can be used to house beam 318 and related structure, as will be discussed with regard to FIG. 3. Ring plate 220 carries ring 222, as will be discussed in further detail herein. Various inserts or sizers can be attached to ring 222 to accommodate various thumb sizes. For example, inserts or sizers can snap on to ring 222, or be secured thereto using, for example, velcro. Ring plate 220 and vertical housing 214 can be secured to top plate 206 using any suitable known securing means, such as bolts 234a, 234b. Alternative means to secure ring plate 220 may optionally be used.

Stationary plate 218 can be interposed between ring plate 220 and top plate 206, and can be secured to ring plate 220 and top plate using any suitable securing means, such as bolts 236. Bolts (not shown) that protrude through top plate 206 can be used to secure a bottom portion of stationary plate 218 to top plate 206. A user's hand is positioned between hand plate 216 and stationary plate 218, with the palm of the user's hand contacting stationary plate 218, and the back of the user's hand contacting hand plate 216. Hand plate 216 can optionally have a soft material affixed thereto, such as foam, cloth, and the like, to increase user comfort. Alternative structures to position the user's hand may optionally be used.

Push plate 212 mates or is connected to a first end of a plurality of tubes 224. A second end of the plurality of tubes 224 mates or is connected to a proximal face (e.g., closest to handle 228) of hand plate 216. Handle 228 is threaded to engage bolt 226 such that when handle 228 is turned in a first direction (e.g. clockwise), push plate 212, tubes 224 and hand plate 216 move toward stationary plate 218 to secure a user's hand, which is positioned between hand plate 216 and stationary plate 218, in a substantially fixed position. When handle 228 is turned in a second direction (e.g., counterclockwise), push plate, tubes 224 and hand plate 216 can be moved away from the user's hand, and thereby permit removal of the hand. Tubes 224 are preferably arranged with respect to push plate 212 and hand plate 216 in a manner such that each tube bears substantially the same load when hand plate 216 engages a user's hand. Pivot 240 will be described with regard to FIG. 3.

Figure 2A:
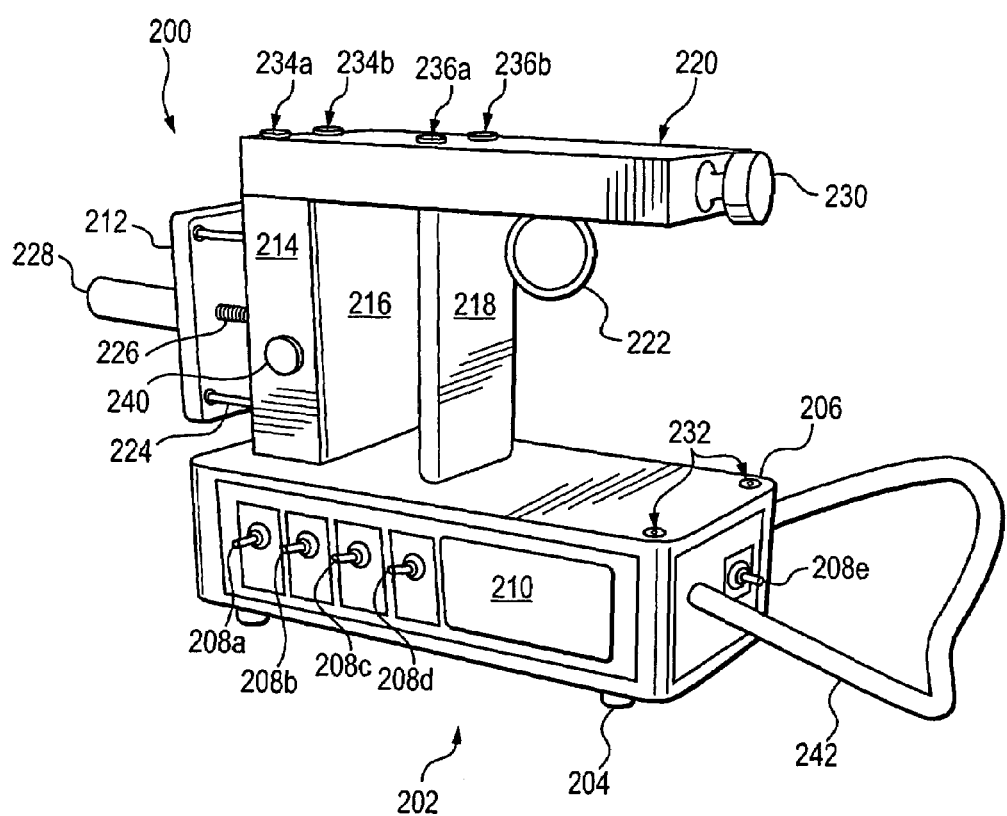
FIG. 2A is a first perspective view of an exemplary apparatus in accordance with the present invention.
Figure 2B:
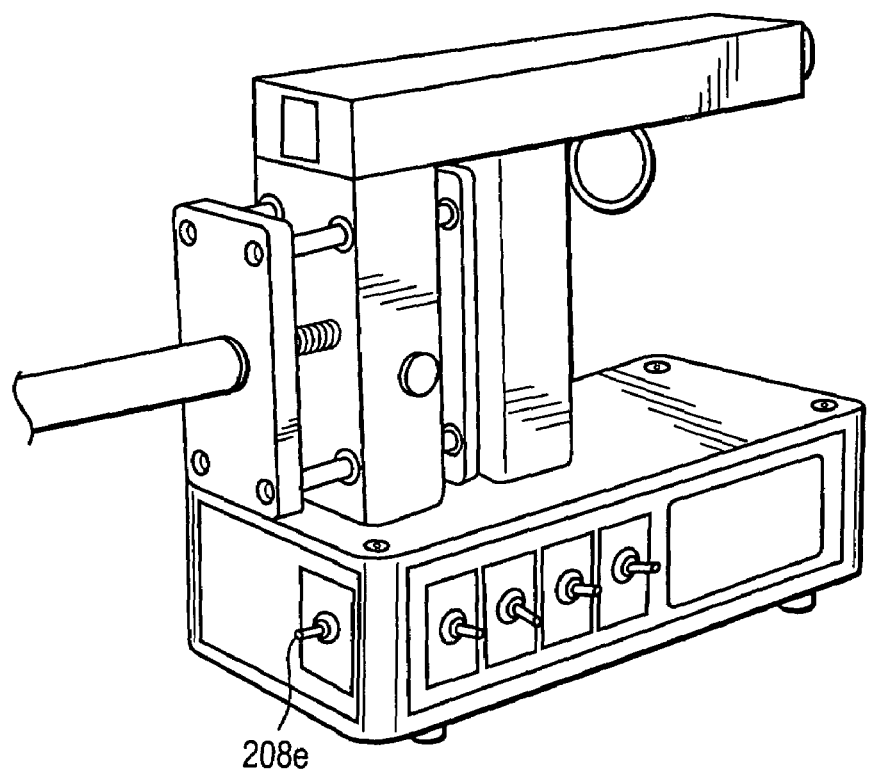
FIG. 2B is a second perspective view of the apparatus shown in FIG. 1A.
Figure 3:
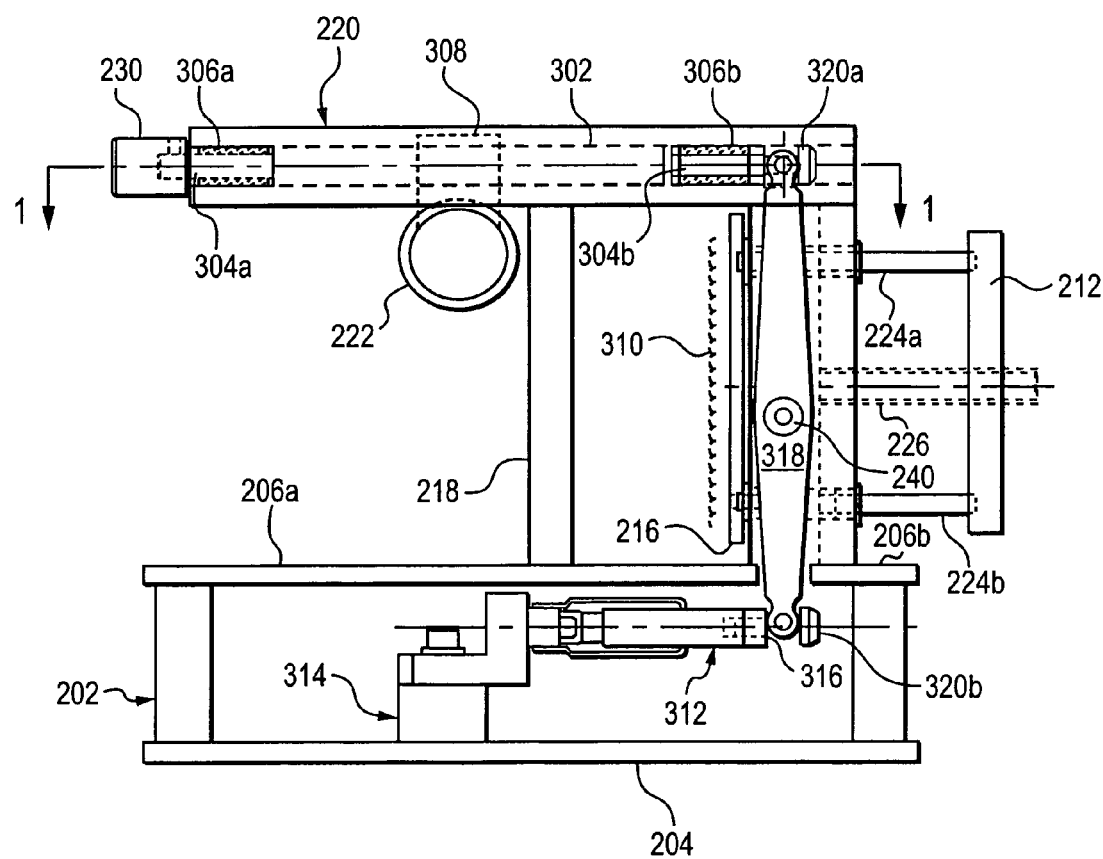
FIG. 3 is a side view of the apparatus shown in FIGS. 2A and 2B.
Figure 4:
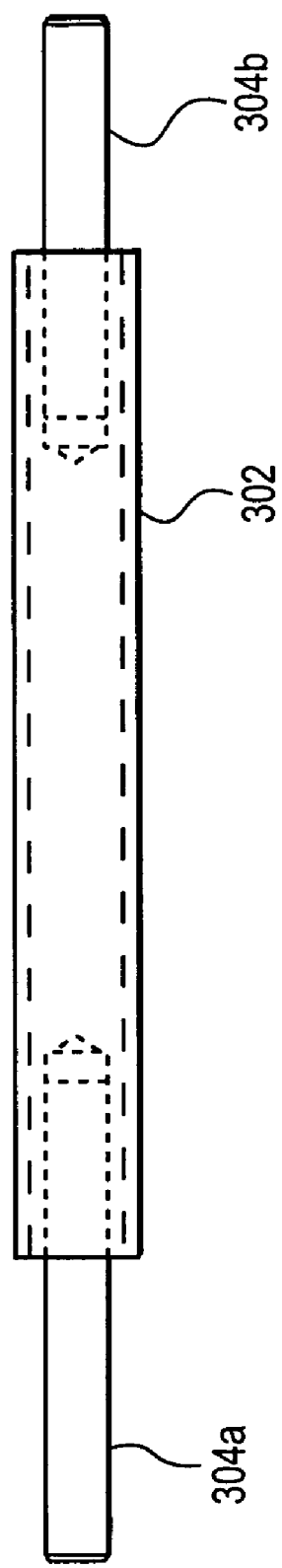
FIG. 4 is an exemplary embodiment of a shaft that can be utilized in connection with the present invention.

FIG. 3 is a side view of the apparatus shown in FIGS. 2A and 2B. Shaft 302 can be a threaded shaft that engages bolt 308. Ring 222 can be secured to bolt 308 in a conventional manner. For example, corresponding holes can be provided in bolt 308 and ring 222 such that ring 222 can be secured to bolt by a rivet or threaded connection. Bearing shafts 304a, 304b are also engaged with shaft 302. A more detailed figure of shaft 302 and bearing shafts 304a, 304b is shown in FIG. 4. Shafts 302, 304a, 304b can be stainless steel. Shaft 302 can have holes drilled for bearing shafts 304a, 304b, and bearing shafts 304a, 304b can be secured to shaft 302 using, for example, a Loctite® adhesive.

Ball bushings 306a, 306b respectively receive shafts 304a, 304b. Knob 230 is connected to bearing shaft 304b such that when knob 230 is turned in a first direction (e.g. clockwise), bolt 308 moves in a first direction (e.g., toward knob 230). When knob 320 is turned in a second direction (e.g., counterclockwise), bolt 308 moves in a second direction (e.g., away from knob 230). Knob 230 thus facilitates adjusting the position of ring 222.

A first end of beam 318 is operatively engaged with or affixed to bearing shaft 304b. A second end of beam 318 is operatively engaged with or affixed to shaft 316 which, in turn, is operatively engaged with or affixed to load cell 312. Load cell 312 can house electronics such as shown in FIGS. 11–14. Mount 314 can be secured to bottom plate 204, and a portion of load cell 312. Caps 320a, 320b can be respectively secured to an end of bearing shaft 306b and shaft 316 to facilitate holding beam 318 substantially in place. Padding 310 is shown contacting hand plate 216. Top plate portions 206a, 206b are shown, which provide a space for beam 318. Shaft 240 is provided to enable the force by the user's thumb received at an upper portion 318a of beam 318 to transfer to a lower portion 318b of beam 318, and subsequently to load cell 312.

In operation, the apparatus 200 is configured so that a hand (not shown) is held in a neutral position in the pronation-supination plane. The user can sit with his or her hand inserted between hand plate 216 and stationary plate 218. The hand can be inserted until the mid-palmar crease of the hand reaches plate 218. The thumb is inserted into thumb ring 222, which can be adjusted to be positioned at a desired distance from plate 218.

Handle 228 can be rotated to secure plate 216 against the hand. Thumb ring 222 can be attached to nut 308 which, in turn, is secured to shaft 302. Thumb ring 222 can be adjusted toward or away from stationary plate 218 by turning adjustable knob 230. For example, turning knob 230 can rotate shaft 302 such that nut 308 can negotiate shaft 302 as it is turning. Accordingly, the position of nut 308 and thumb ring 222 can be adjusted within the stationary plate 218.

Figure 15:
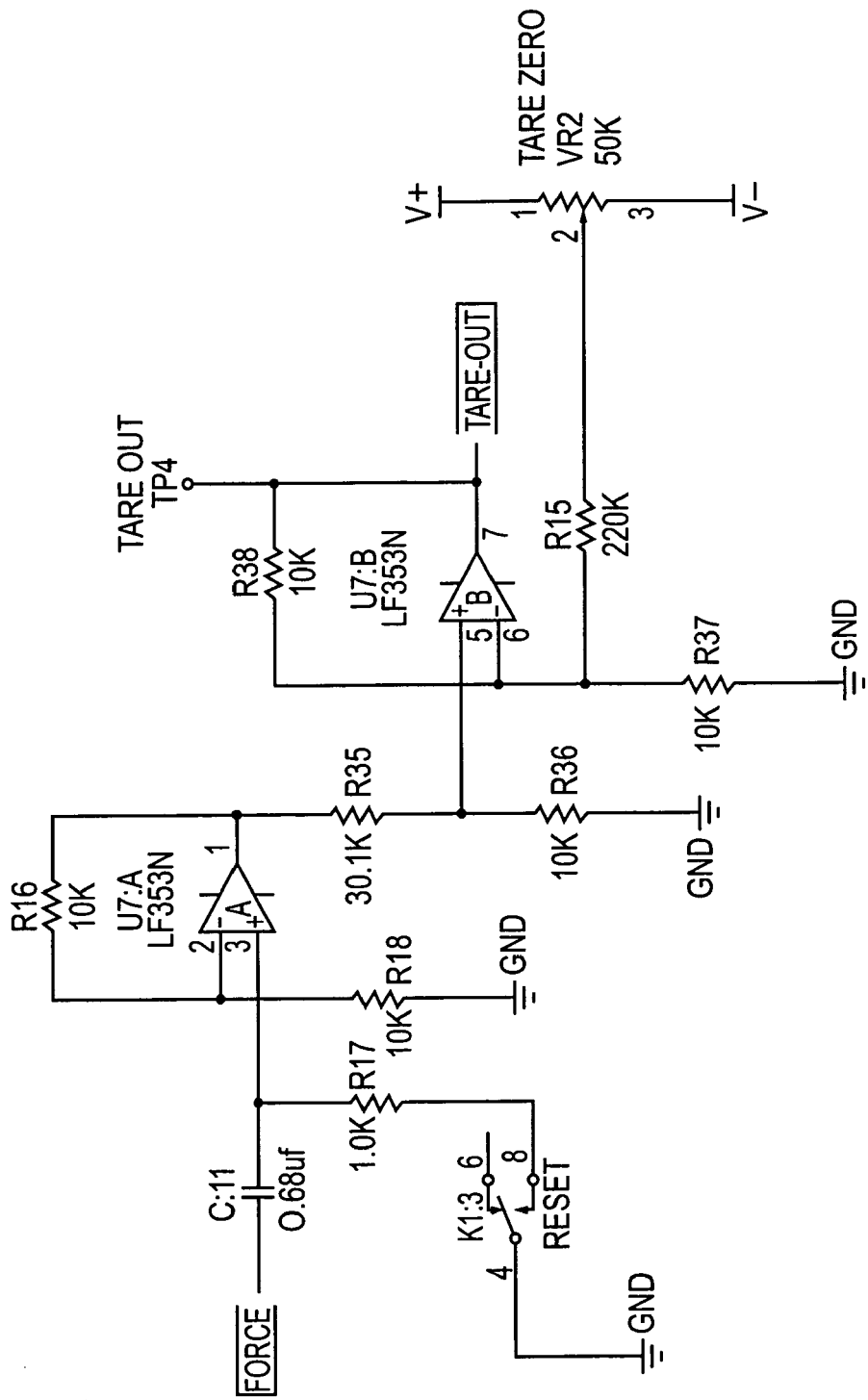
FIG. 15 shows various exemplary electronics that can be used with force measurement in connection with the present invention.

Shaft 302 is operatively configured to operate with a strain gauge, or similar force measuring device, within load cell 312 to record forces generated by the thumb. In an embodiment, there is no observable movement in ring 222 (and thus shaft 302 and/or beam 308) when thumb force is exerted by a user. Load cell 302 can be supplied with a constant low voltage, which is nulled by adjustment circuitry such as shown in FIG. 15 when no thumb force is present. When thumb force is applied, there is an output voltage change, positive or negative, which is amplified and converted to a digital readout showing force, as pounds or kilograms, in display 202.

Depending on the position of adjustable ring 222, different forces can be generated by the thumb. Accordingly, there is a distance of ring 222 from the hand that enables the thumb to generate maximum forces. Forces generated by the thumb are transferred to shaft 302, 306*a*, 306*b*, and to load cell 312.

In addition, display 210 or the display (not shown) on the opposing side of base 202 can optionally be blacked out by using switch 208*a*, so that the user does not see the display of thumb force generated during. Display 210 can be a digital display, optionally connected with, for example, a Windows®-based software program that can plot a "force versus time" curve to detect muscle fatigue. For example, cable 242 can be used to transmit recorded forces to a Windows®-based software program that can plot, for example, a force versus time curve.

Deviations from normal measurement can be used to assess differing disease states, such as in carpal tunnel syndrome and/or isolated injuries to, for example, the median and/or ulnar nerve.

It is preferred that the wrist is held at 350 of extension, and that the palmar digits are kept in full extension at the metacarpal-phalangeal (MP), proximal interphalangeal (PIP), and distal interphalangeal (DIP) joints. The thumb can be positioned at the level of the inter-phalangeal joint, and then inserted into the ring 222. The static angle of thumb abduction can be assessed with a goniometer at, for example, 30, 45 and 60 degrees. Other degrees of extension are also possible, for example, ranging between 15 degrees and 55 degrees, or full extension and/or flexion.

Figure 5:
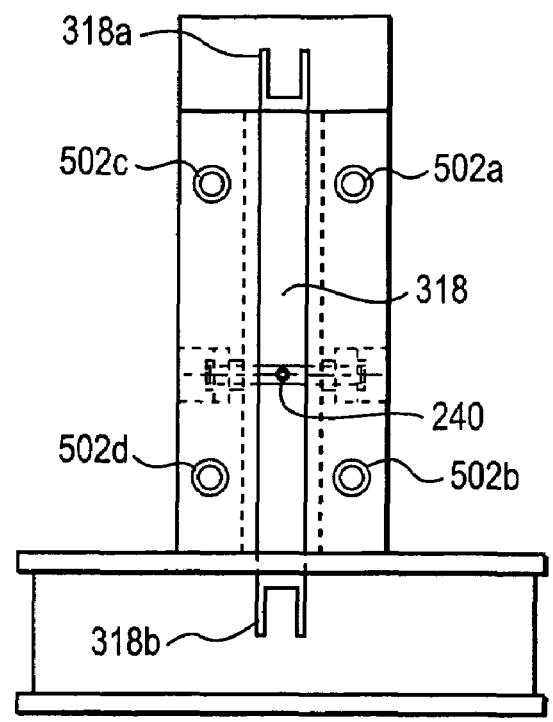
FIG. 5 is an end view of FIG. 3.

FIG. 5 is an end view of FIG. 3, showing beam 318. Tube holes 502*a*–*d* are shown, which respectively receive or contact a tube 224, as shown in FIGS. 2A and 2B.

Figure 6:
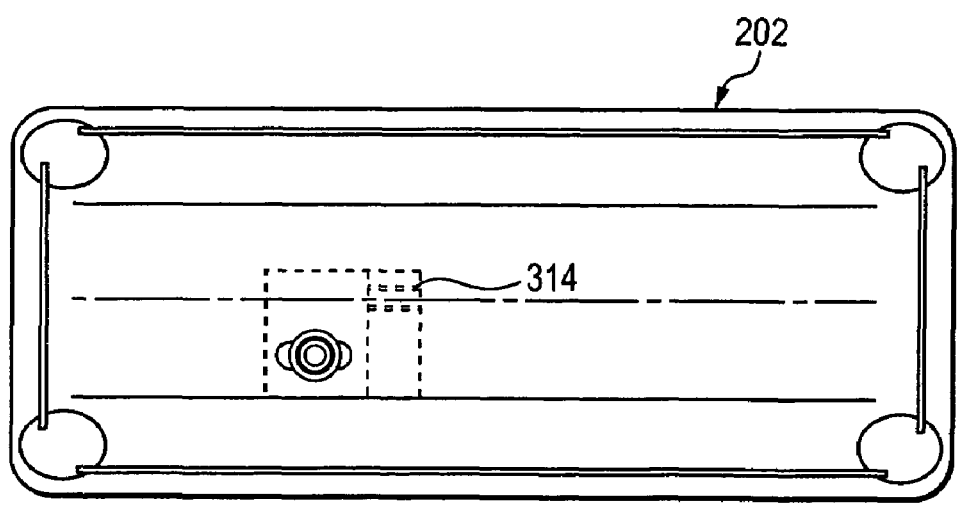
FIG. 6 is a top sectional view of FIG. 3, showing a load cell mount.

FIG. 6 is a top sectional view of FIG. 3, showing an exemplary positioning of load cell mount 314 within base 202.

FIG. 7A is a top sectional view of ring plate 220, viewed in the direction of cut 1—1 as shown in FIG. 3. FIG. 7B is an elevation view of ring plate 220. Spaces 704*a*, 704*b* are respective spaces for ball bushings 306*a*, 306*b*. Space 702 receives shaft 302 and bolt 308. Space 706 receives the top portion of beam 318 and cap 320*a*.

Figure 8A:
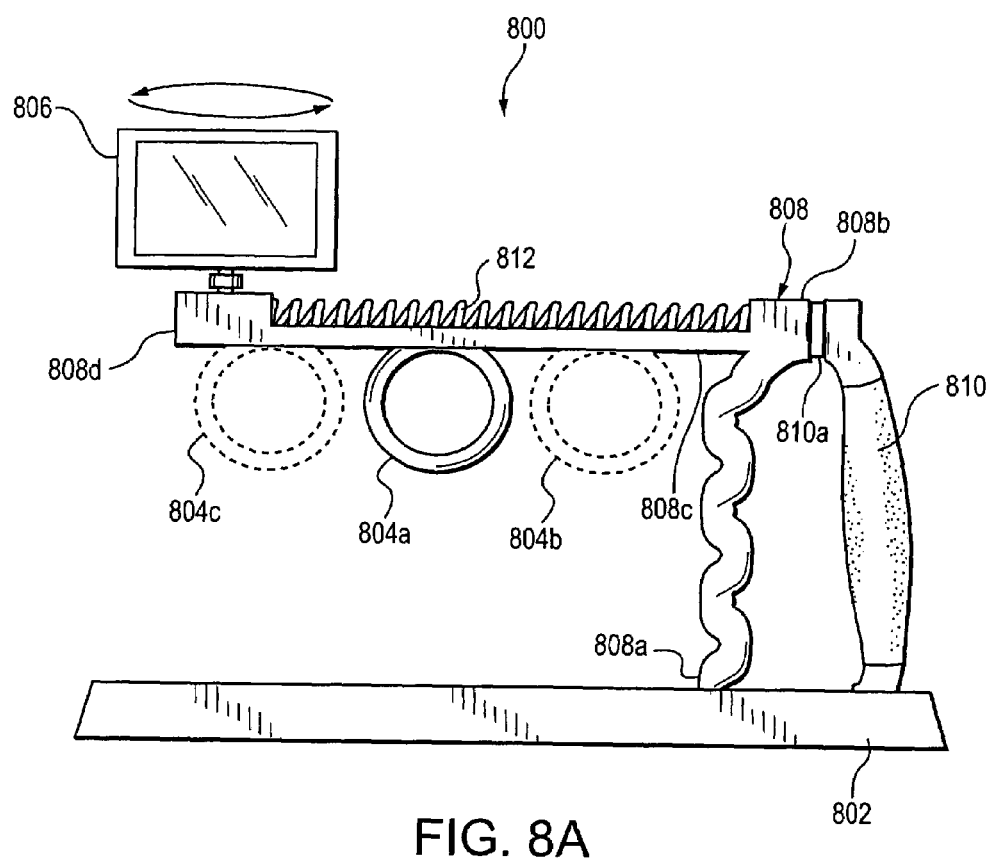
FIGS. 8A and 8B show a second exemplary embodiment of the present invention.
Figure 8B:
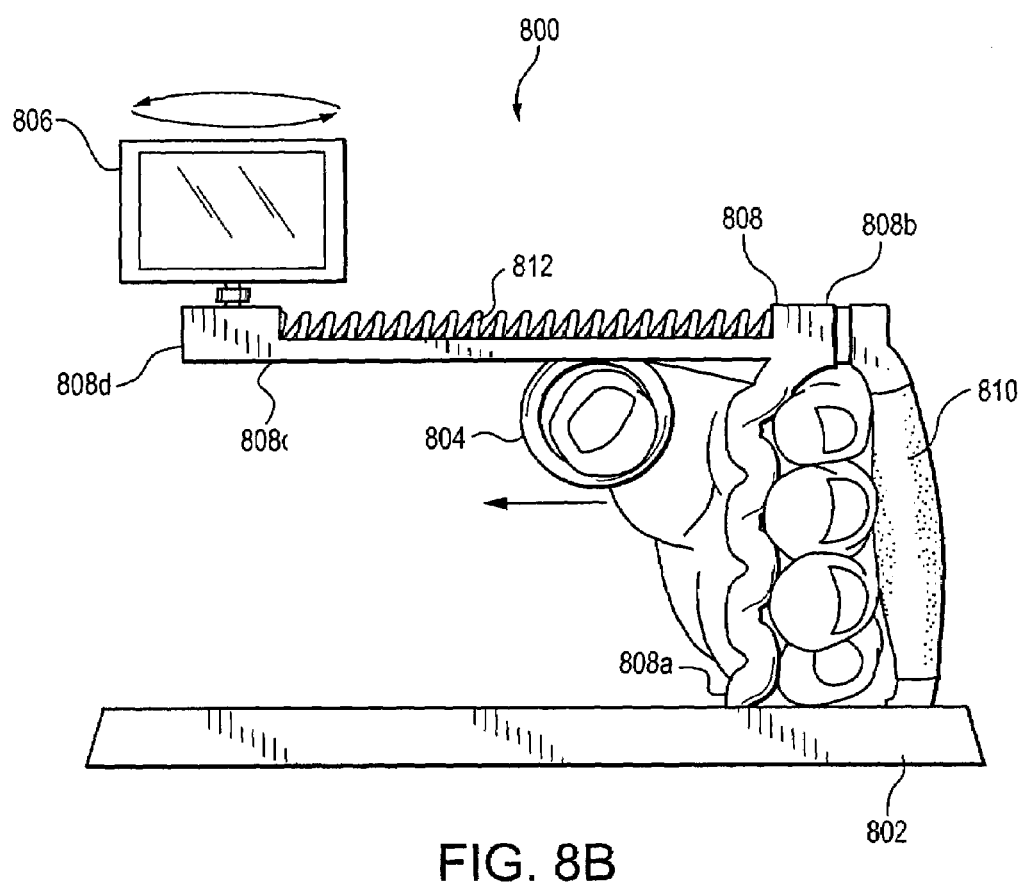

FIGS. 8A and 8B, generally at 800, show a second exemplary embodiment of the present invention. Platform 802 is provided, which contacts a lower portion 808*a* of stationary hand rest 808. An interface portion 808*b* of hand rest 808 can receive an extended portion 810*a* of moveable hand rest 810. Extended portion 810*a* can also be a piece that is separate from hand rest 810. Extended portion 810*a* can optionally move into and away from interface 808*b* to secure a user's hand, as shown in FIG. 8B.

Spring guide 808*c* is positioned between interface 808*b* and mount 808*d*. Standard electronics similar to that shown in FIGS. 10–15, and related structure can be housed in mount 808*d*. The force exerted by the user's thumb on ring 804*a* can be displayed on display 806. Ring 804*a* can be connected to spring 812 in various positions, as shown at 804*b*, 804*c*. In the embodiment shown in FIGS. 8A and 8B, spring 812 can be used in lieu of bearing shafts 304*a*, *b* and respective ball bushings 306*a*, 306*b*, and bolt 308 shown, for example, in FIG. 3. Spring 812 preferably has a sufficiently high spring constant such that no visible movement of spring 812, and thus ring 804*a*, is apparent when a user exerts force on ring 804*a*.

The forces created in the spring is transferred to a load cell and calibrated strain gauge (not shown), which can be housed in display mount 808*d* in a manner similar to that shown in FIG. 3. Switches (not shown) can be provided in a manner similar to that shown, for example, in FIGS. 2A and 2B to select the direction in which thumb force is being applied, select force measurement in either pounds or kilograms, select a peak force, and/or select a continuously updated display of measured force. In addition, display 806 can be selectively blacked out so that apparatus 800 can be used in a blinded fashion with respect to the patient. Display 806 can be connected to and/or configured to operate with, for example, a Windows®-based software program, optionally running on a separate computing device, that can plot, for example, a thumb force versus time curve.

Figure 9:
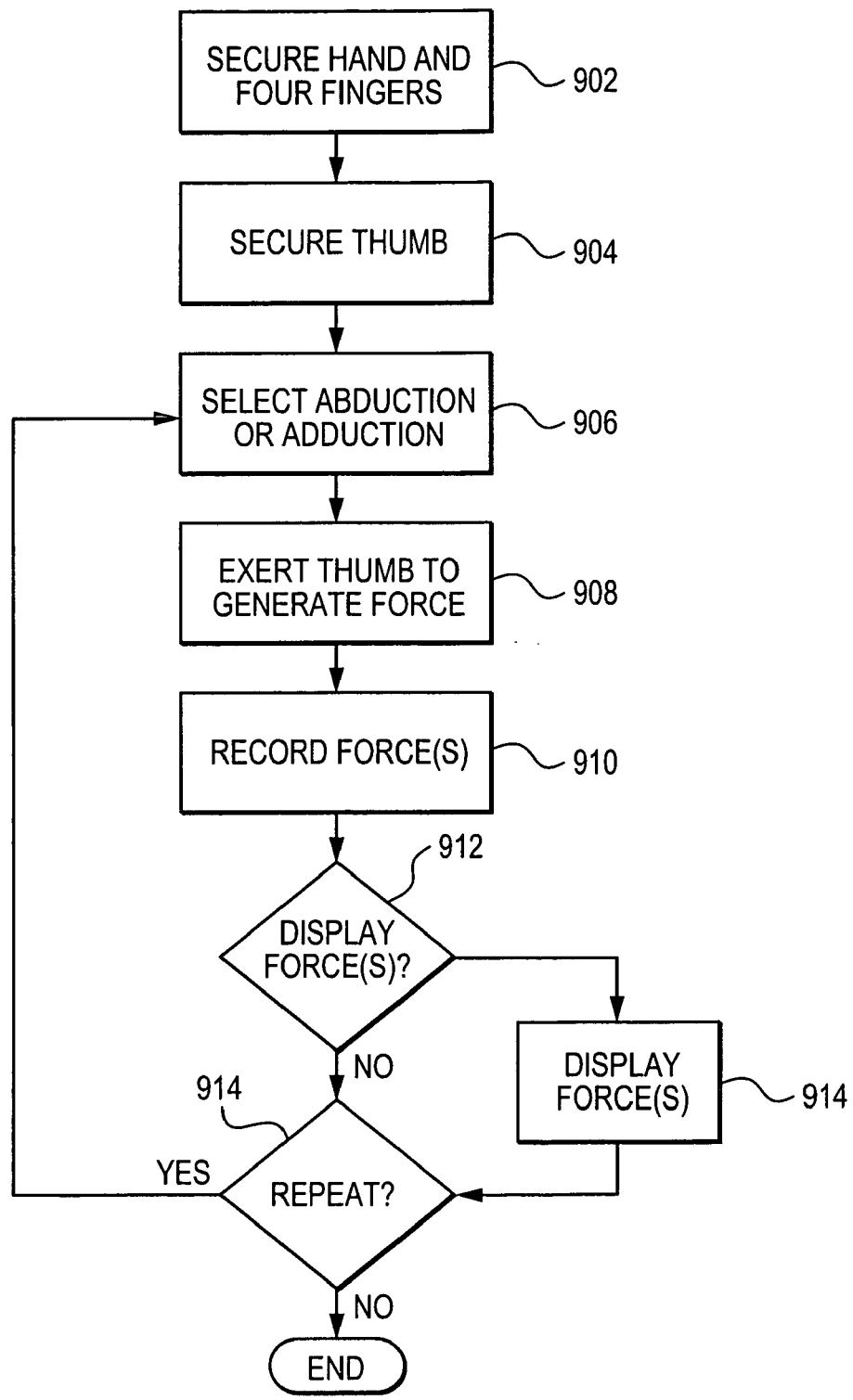
FIG. 9 is a flow diagram of an exemplary method in accordance with the present invention.

FIG. 9 is a flow diagram of an exemplary method in accordance with embodiments of the present invention. The method described with regard to FIG. 9 is also applicable to the embodiment shown in FIGS. 8A and 8B, but will be described with regard to FIGS. 2A and 2B. Note that the method described in FIG. 9 is exemplary, and may performed in different orders and/or sequences as dictated by the apparatus of the present invention, and any alternative embodiments of the apparatus. In addition, the method described herein is not limited to the specific use of the apparatus of the present invention, but may be performed using any apparatus that is capable of obtaining the information as described in connection with the apparatus of the present invention.

At step 902, a user positions his hand and four fingers in the apparatus 300, between hand plate 216 and stationary plate 218 shown in FIGS. 2A and 2B. Other sequences of the method are also within the scope of the present invention.

At step 904, the user's thumb is positioned in ring 222 and, at step 906, the abduction or adduction mode is selected. At step 908, the user exerts thumb force and, at step 910, the forces by the thumb are recorded. At decision step 912, a determination is made whether to display the force(s) on display 210. If the forces are to be displayed, at step 914 the forces can be displayed on display 220. If at decision step 912 it is determined that forces are not to be displayed, and after step 914, a determination is made whether to perform an additional force measurement. If another force measurement is performed, the process returns to step 906. If no additional force measurements are to be taken, the process ends.

Figure 10:
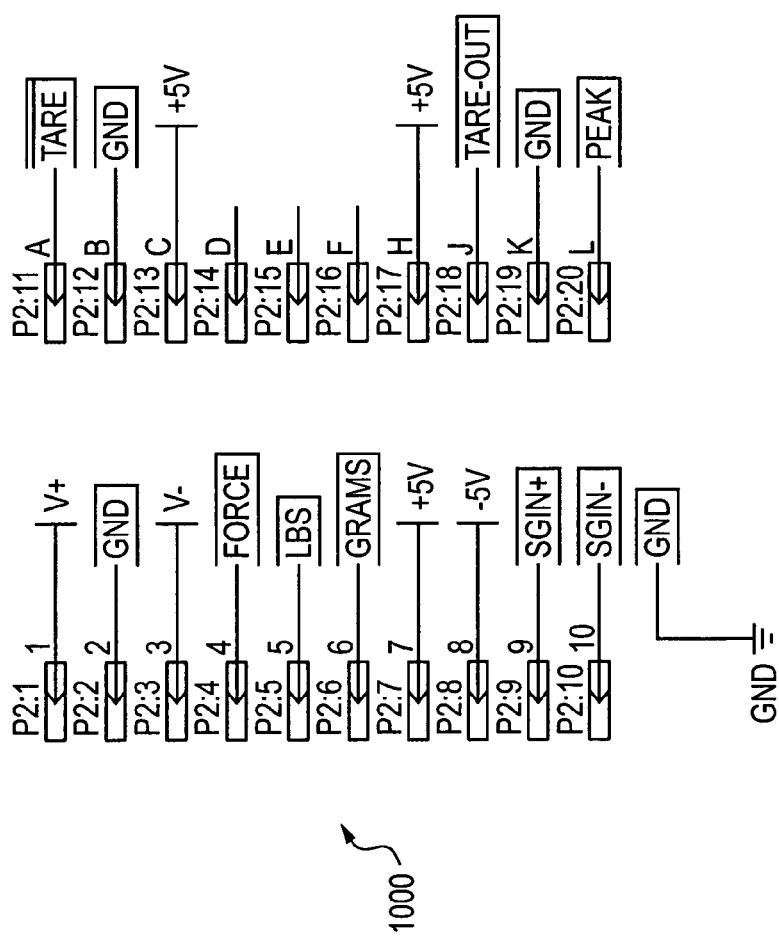
FIG. 10 is an exemplary circuit diagram of an edge connector that can be used in connection with the present invention.

FIG. 10, generally at 1000, is an exemplary and standard circuit diagram of an edge card 1000 connector that can be used in connection with a personal computer (not shown) that receives data from the apparatus 200, 800. Cable 242 connected to apparatus 200, 800 can interface with the edge card 1000 to transfer data to the computer.

Figure 11:
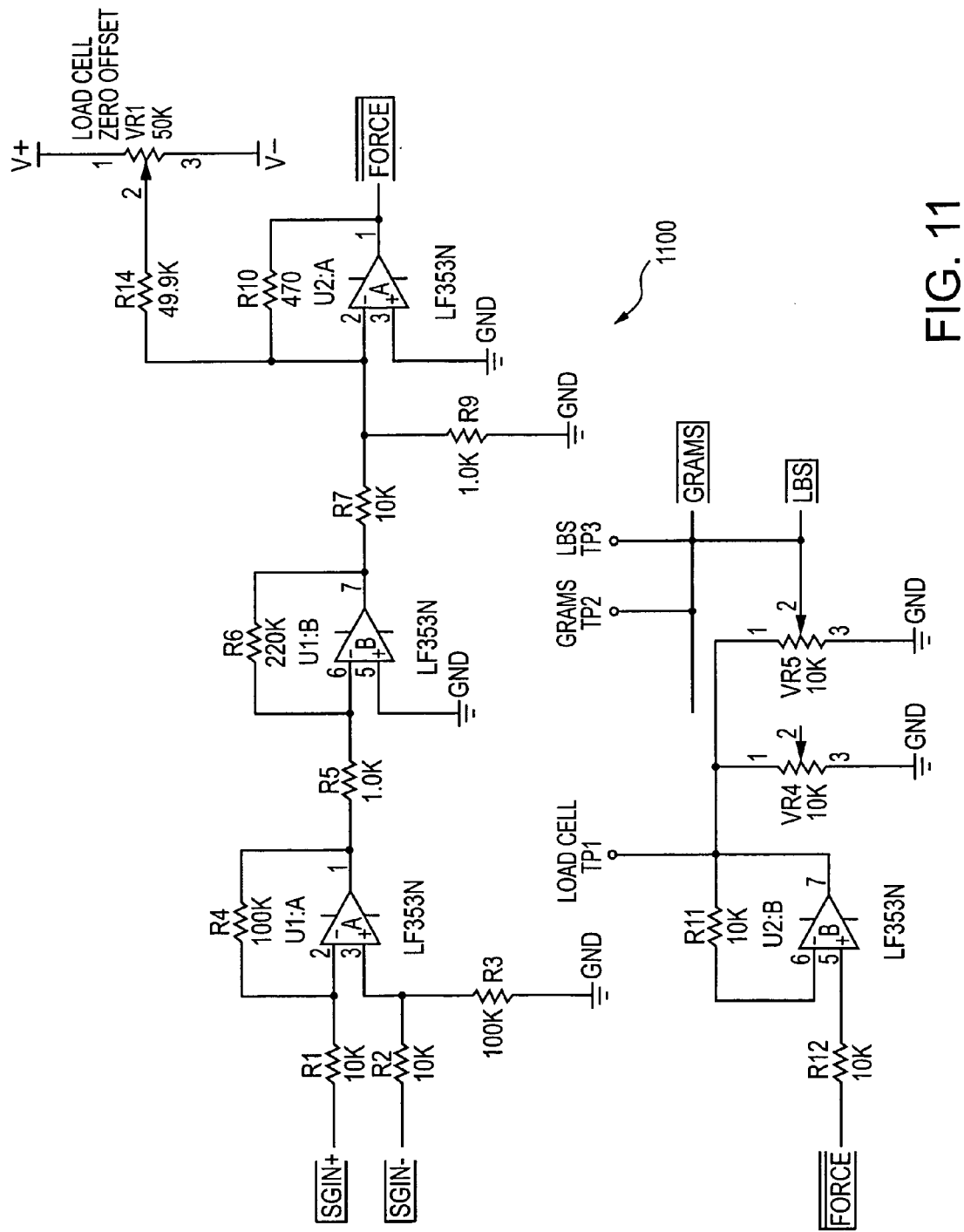
FIG. 11 is a diagram of exemplary force circuitry that can be used in connection with the present invention.

FIG. 11, generally at 1100, is a diagram of exemplary and standard force circuitry that can be used in connection with the present invention to record forces generated by a user's thumb. The circuitry can be located in load cell 312.

Figure 12:
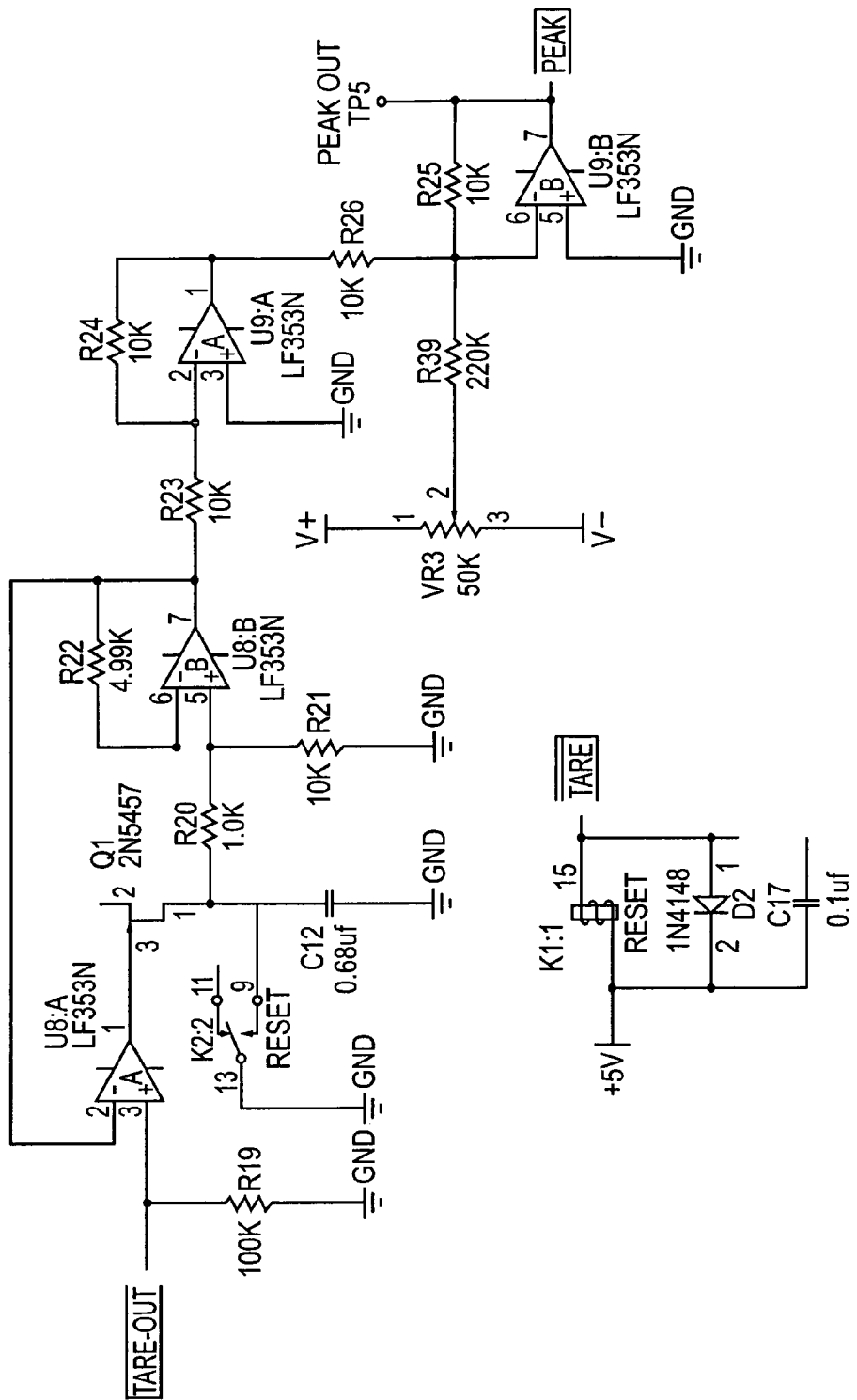
FIG. 12 is a diagram of exemplary auto tare circuitry that can be used in connection with the present invention.

FIG. 12 is a diagram of exemplary and standard circuitry that can be used to record peak forces generated by a user's thumb. The circuitry can be located in load cell 312.

Figures 13, 14:
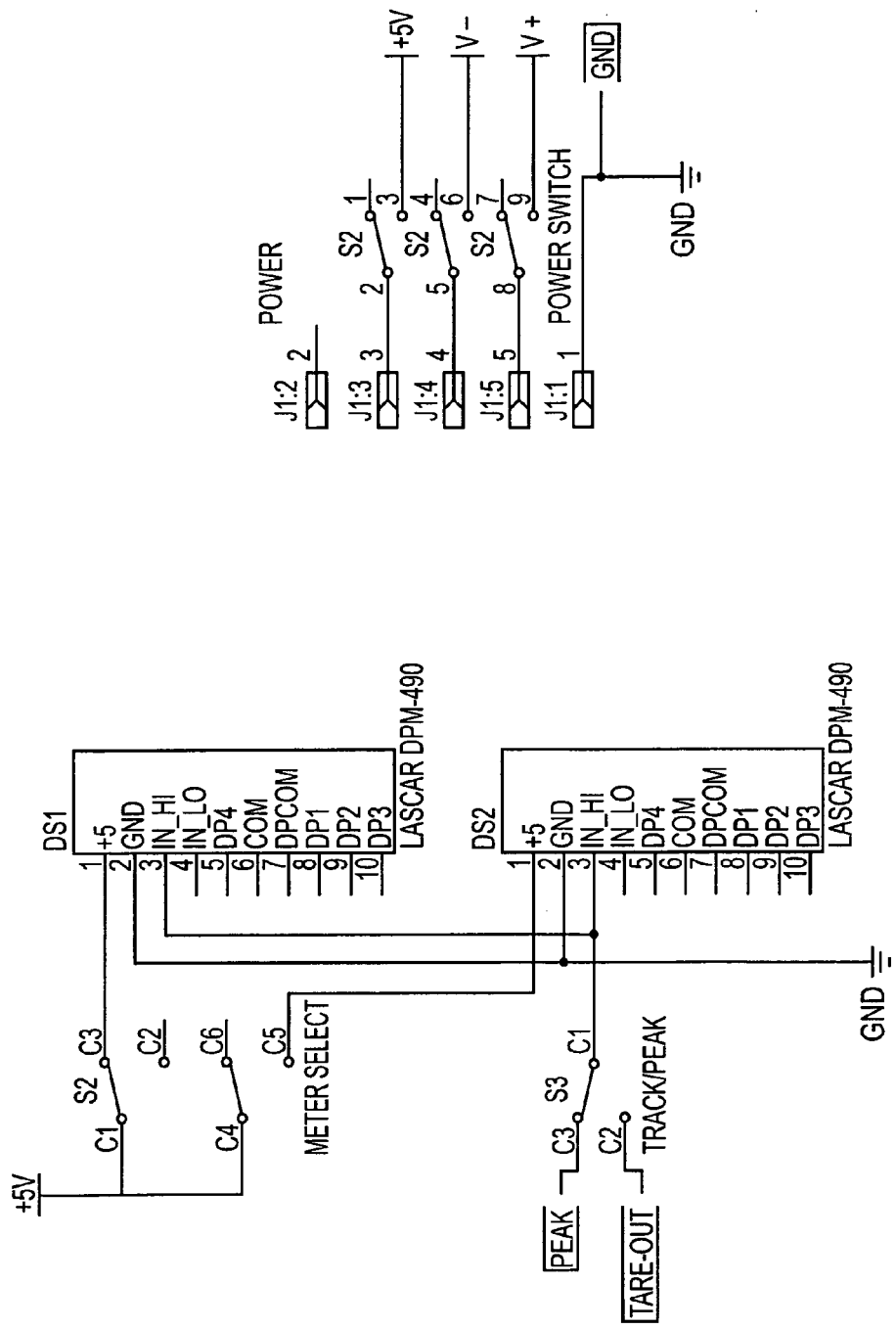
FIG. 13 is a diagram of exemplary peak hold circuitry that can be used in connection with the present invention.
FIG. 14 shows various exemplary electronics that can be used with power activation and deactivation in connection with the present invention.

FIG. 13 is a diagram of exemplary and standard peak hold circuitry that can be used in connection with the present invention. The circuitry can be located in load cell 312.

FIG. 14 shows various exemplary and standard electronics that can be used with power activation and deactivation in connection with the present invention, in connection with switch 208e. The circuitry can be located in load cell 312.

FIG. 15 shows various exemplary and standard electronics that can be used with force measurement in connection with the present invention. The circuitry can be located in load cell 312.

Emperical Testing and Results

Six hundred patients between the ages of ten and seventy years of age were tested using the apparatus 200. Patients were divided into seven age groups according to decade, with equal numbers of males and females. Patients in each age group were stratified according to eight weight classes ranging from fifty to three hundred pounds. Hand dominance as well as the value of mid range grip (third position on the Jamar dynamometer) was recorded. Each subject was asked as to whether they ever had any injuries or surgery to their hand and as to the presence of any symptoms in their hands such as numbness, tingling, weakness or pain in their hands. A positive answer to any of the above questions disqualified the subject from taking the test.

Both hands were then sequentially placed into the apparatus 200, and secured into place. The values for abduction and adduction strength were recorded at the 30, 45, and 60-degree positions, and comparisons between these values are made. Correlations of results as to age, weight, and hand dominance and grip strength were assessed and recorded.

There were two hundred ninety four males of which 93% were right hand dominant. Of the three hundred six females, 91% were right handed. In both groups the numbers of patients were evenly distributed for each age range from 10–70 years old. The vast majority of patients fell within the 125–200 pound weight range (FIG. 16). However it is noted that within each age class there were wide variations in weight. For each parameter of age and weight, a specific mean value for abduction and adduction and grip strength can be assigned (FIGS. 17–20). Using a standard reference manual, one can determine for any age and weight parameter what the mean and standard deviation for grip, adduction, and abduction are and a given patient can be compared against this data.

Grip strength in men increases to a peak between 25–40 years old to 120 pounds, and slowly decreases to 90 pounds by age 75. Within each age class, the grip can vary by as much as 35 pounds, but in general follows the curve of averages (FIG. 21). This holds true for right and left hands.

The curve for females is much flatter than males, with averages from 60–80 pounds. Within each age class there is variability by weight class by as much as 30 pounds. There is no significant difference between right and left hands.

Figure 22:
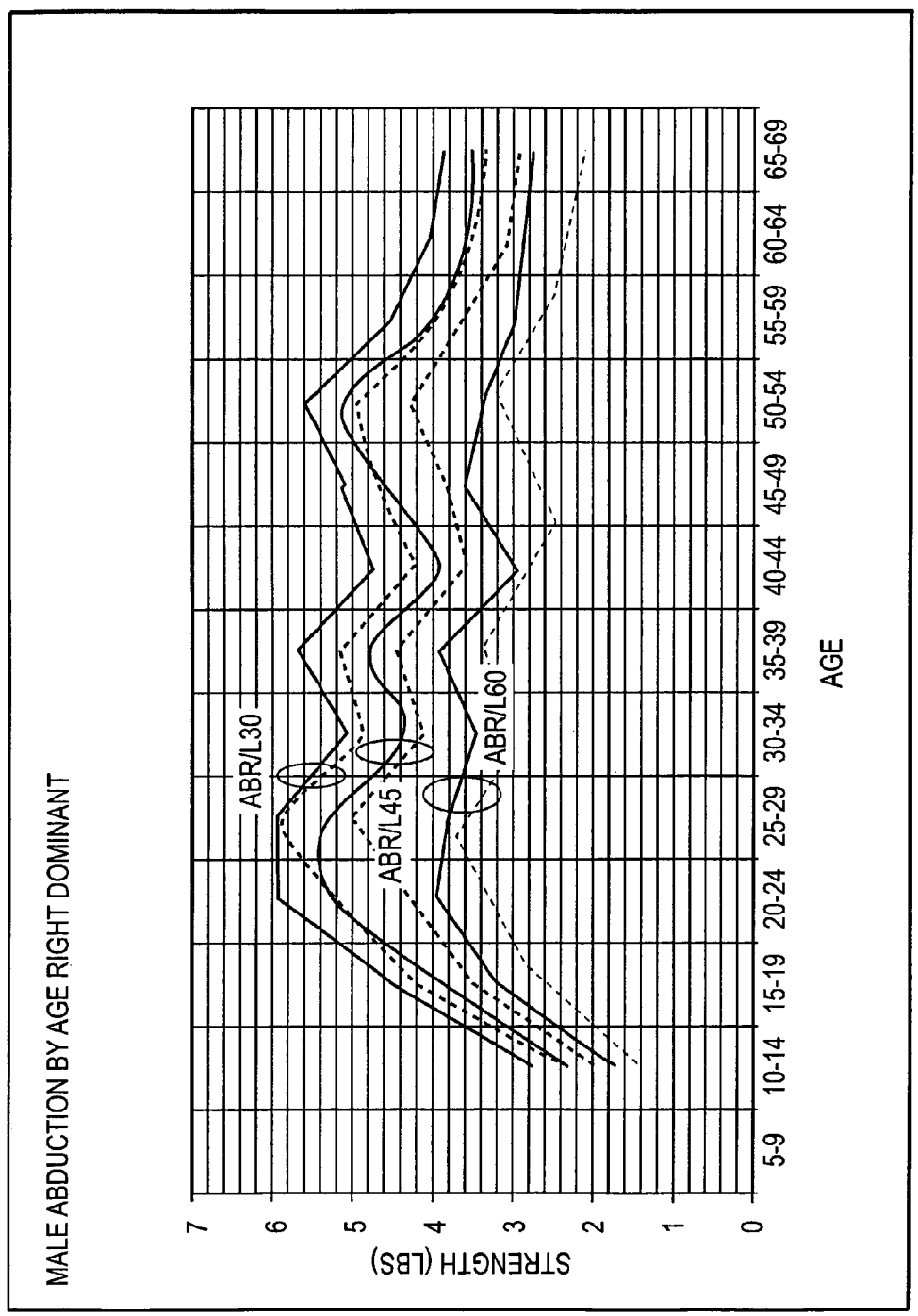
FIG. 22 is a data chart showing right dominant male abduction strength by age at 30, 45 and 60 degree positions.

Looking specifically at abduction as a function of age for males, right hands are consistently but not significantly stronger than left hands. There is a tri-modal curve with peaks at age 25, 37, and 53 years old. At 30° abduction, this approaches 5.8 pounds. The strength of abduction decreases as the starting position of abduction increases from 30 to 45 and to 60 degrees (FIG. 22).

Figure 23:
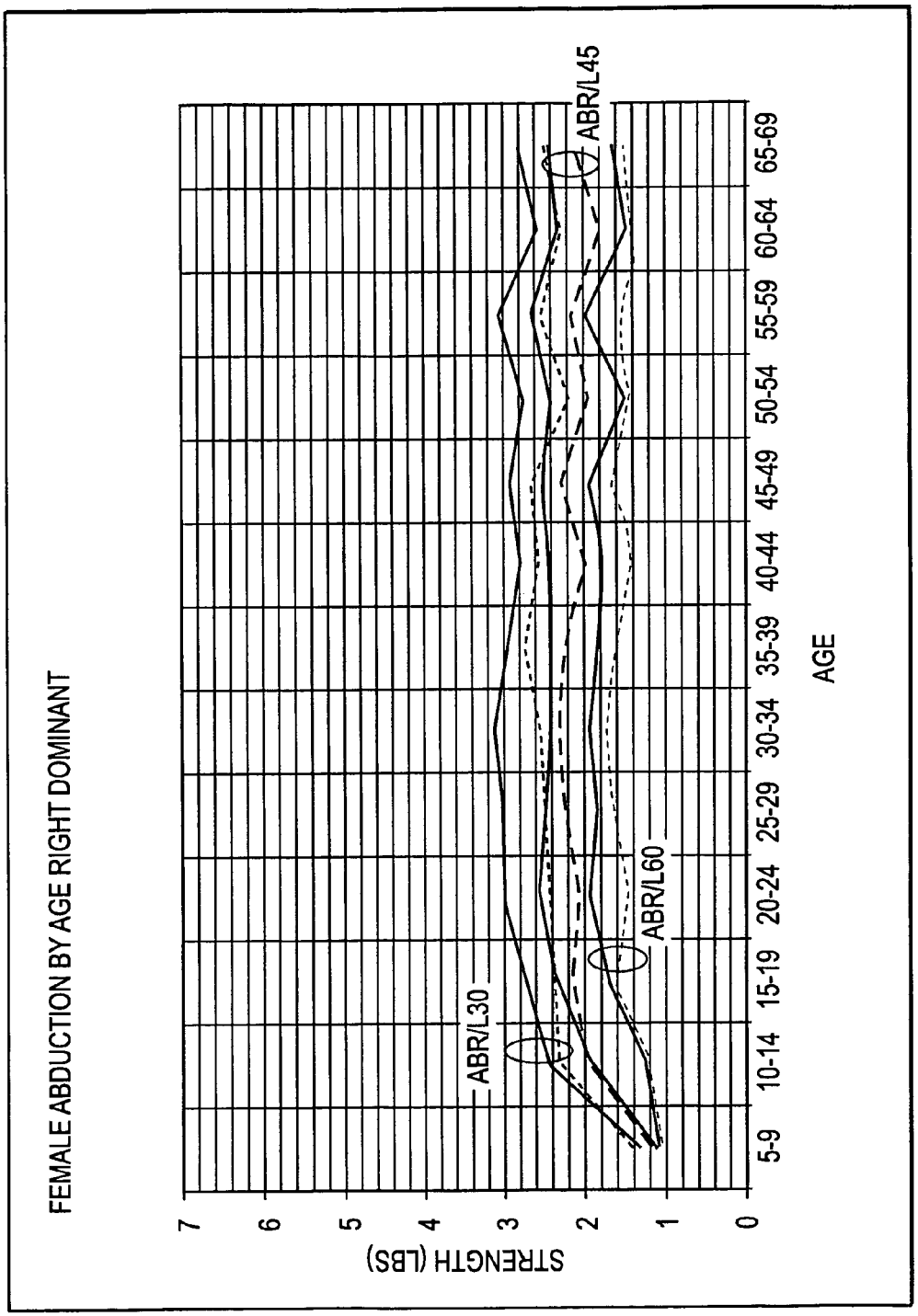
FIG. 23 is a data chart showing right dominant female abduction strength by age at 30, 45 and 60 degree positions.

For females, abduction strength rises to three pounds by age 24, and remains constant throughout life (FIG. 23). The strength of abduction decreases as the starting position of abduction increases. Within each age group there is significant variability according to weight, which is more apparent in males than females.

Figure 24:
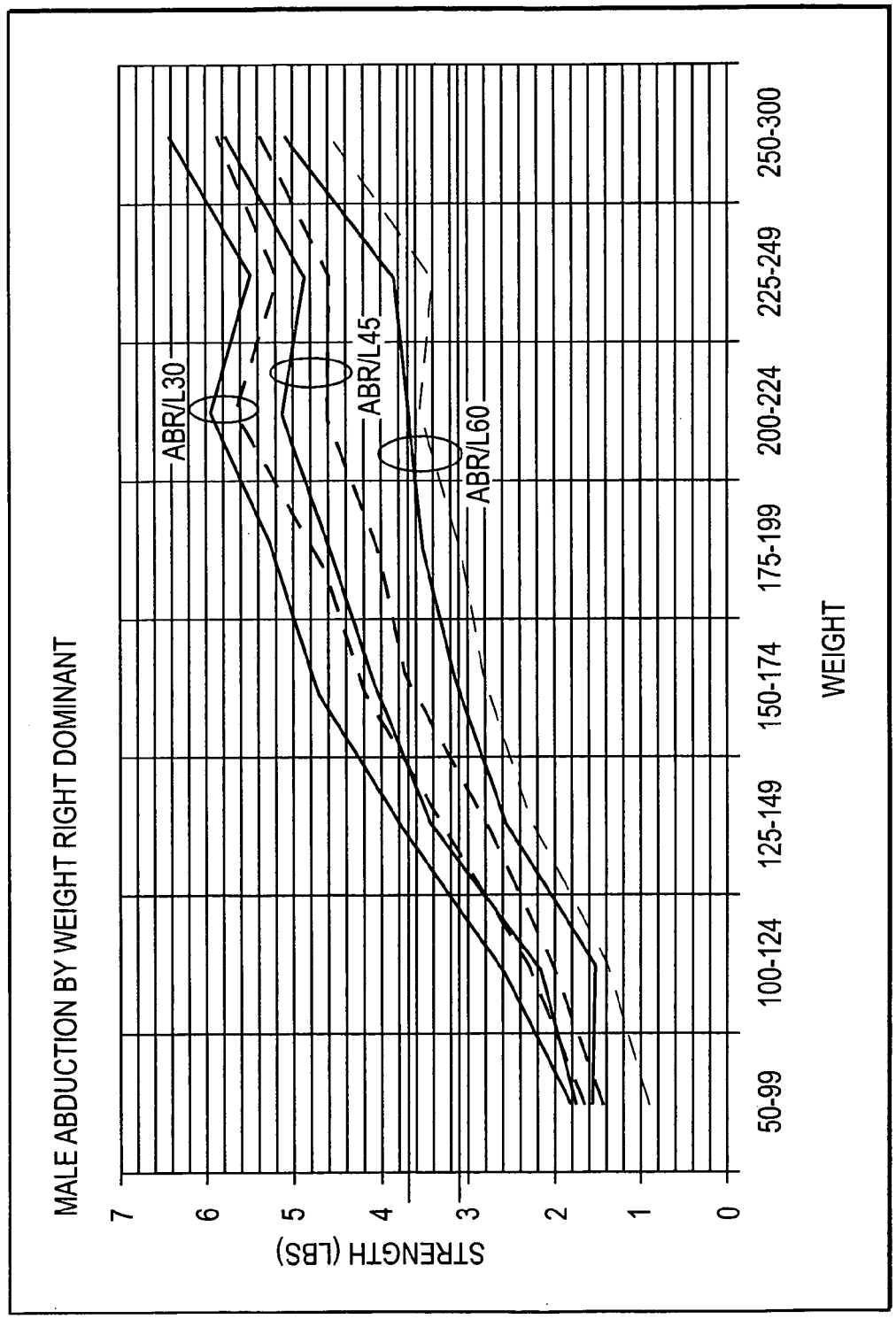
FIG. 24 is a data chart showing right dominant male abduction strength by weight at 30, 45 and 60 degree positions.
Figure 25:
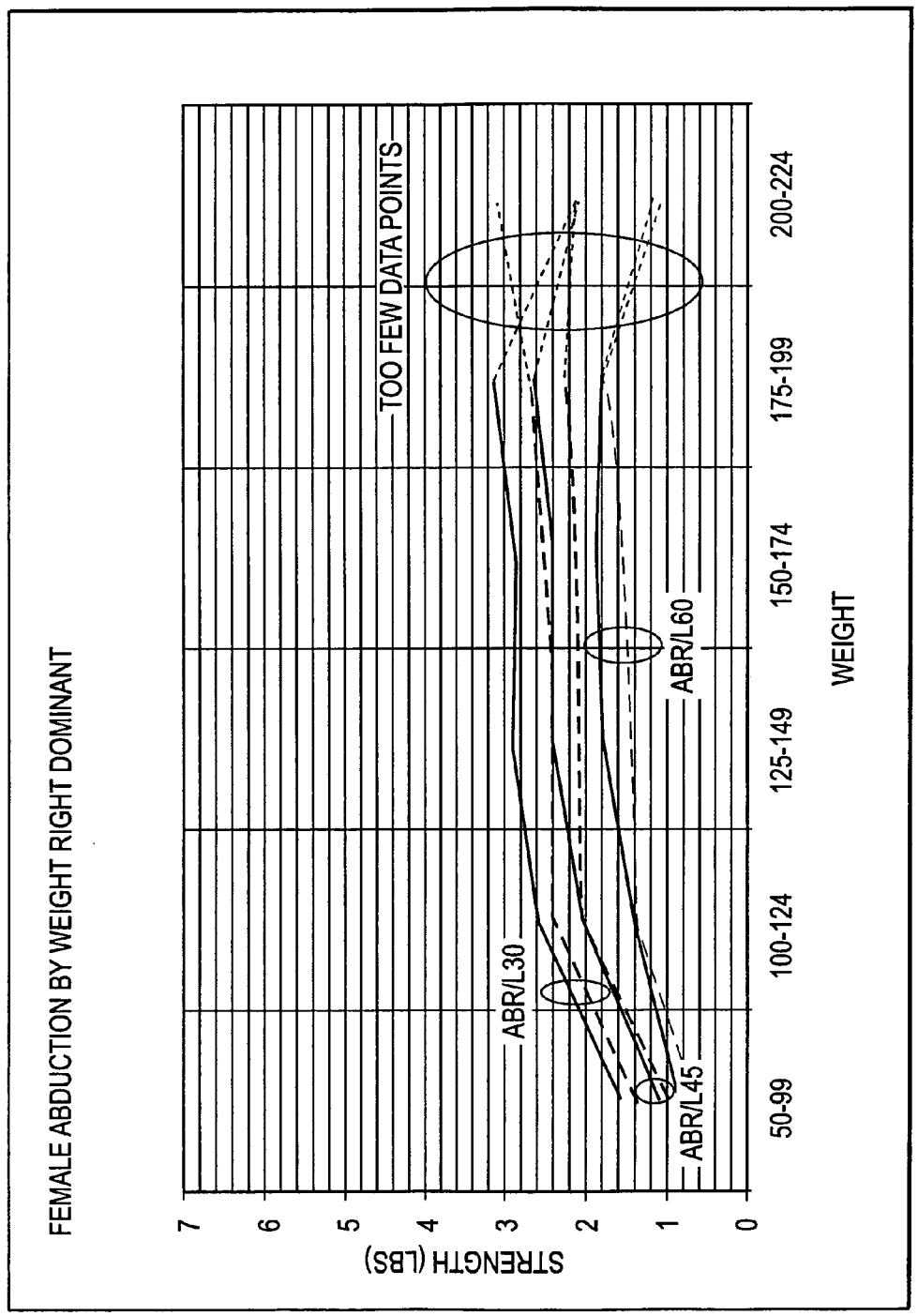
FIG. 25 is a data chart showing right dominant female abduction strength by weight and age at 30, 45 and 60 degree positions.

If the data is broken down according to weight, for males, there is a steady rise in abduction, with weight leveling off at 225 pounds with 6.0 pounds of force. As the starting position of abduction increases from 30 to 45 to 600, the power of abduction diminishes. Also the right dominant hand is stronger than the left hand (FIG. 24). For females, there is a rise in abduction with weight to 3.2 pounds of force, but less dramatic than with males (FIG. 25).

Figure 26:
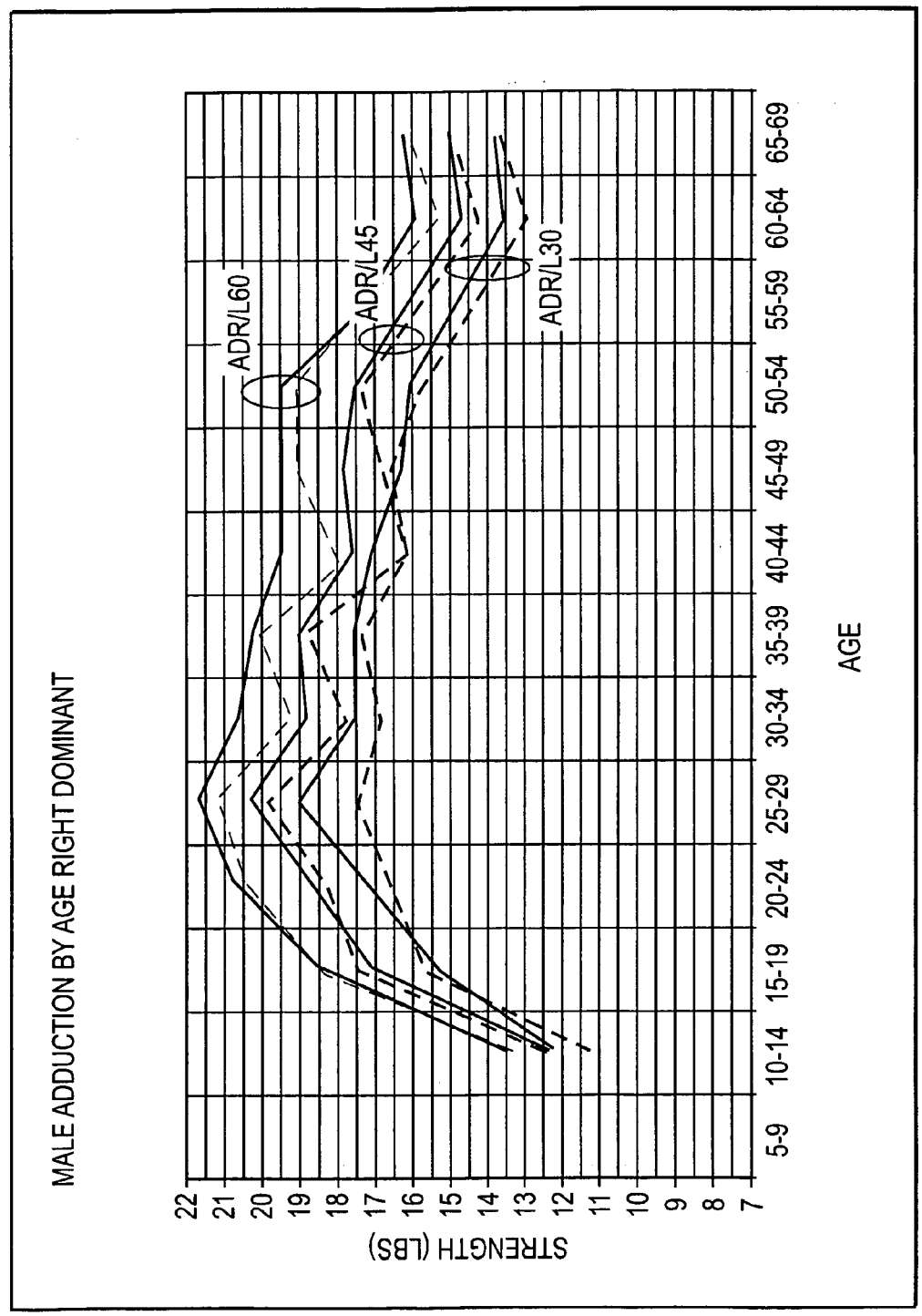
FIG. 26 is a data chart showing right dominant male adduction strength by age at 30, 45 and 60 degree positions.

For male adduction, there is a tri-modal distribution with peaks at 27, 37, and 53 years of age. At 600 thumb abduction angle, maximal adduction strength is 21.5 pounds of force, which occurs at age 27. With increasing abduction angle the strength of adduction increases. The right hand is stronger than the left hand, but not significantly so (FIG. 26).

Figure 27:
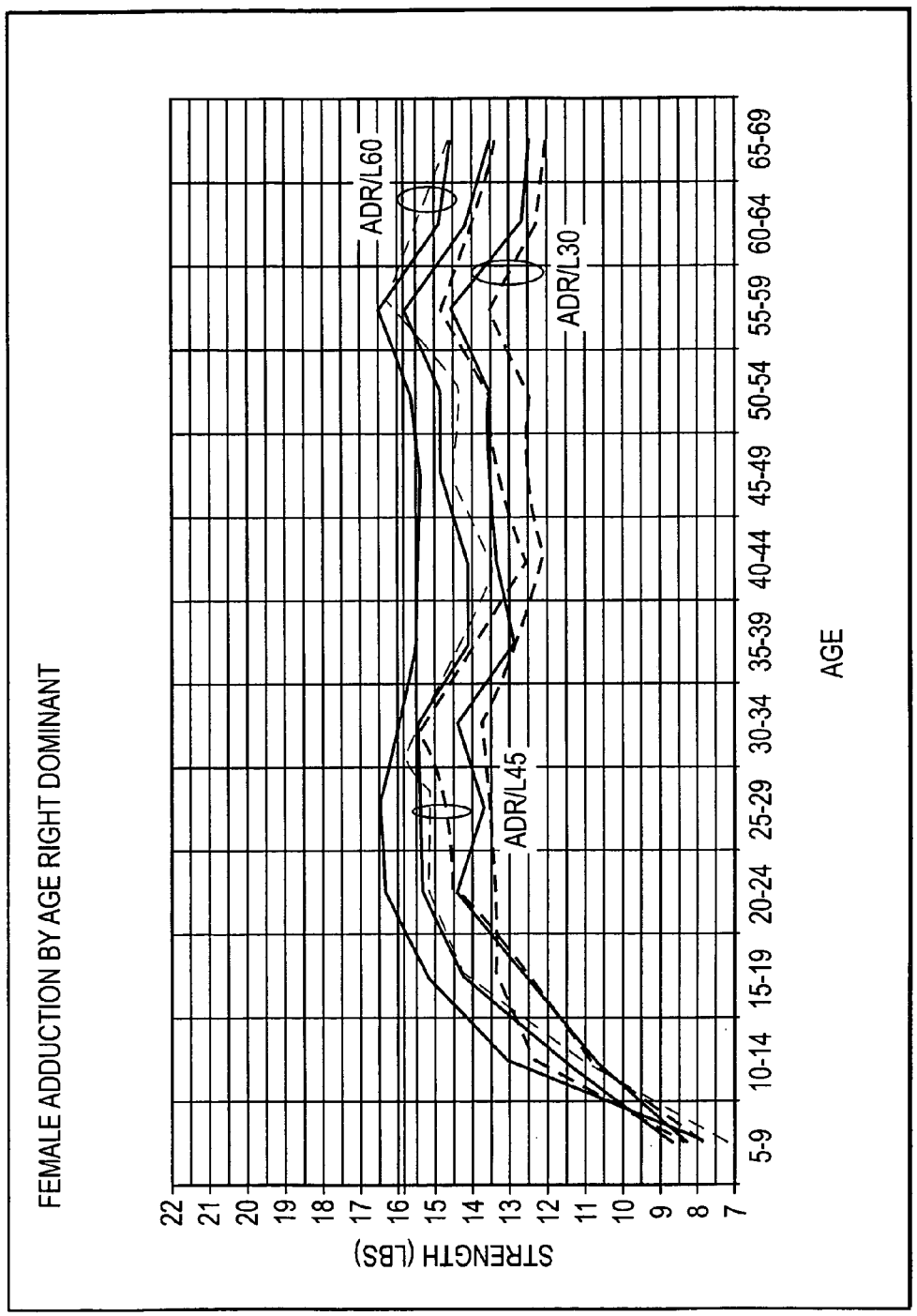
FIG. 27 is a data chart showing right dominant female adduction strength by age at 30, 45 and 60 degree positions.

For females, the curves are flatter thin males after age 24 (FIG. 27). There is increased strength of adduction with increased thumb abduction angle. Peak strength occurs at 55–59 years of age at 16.5 pounds.

Figure 28:
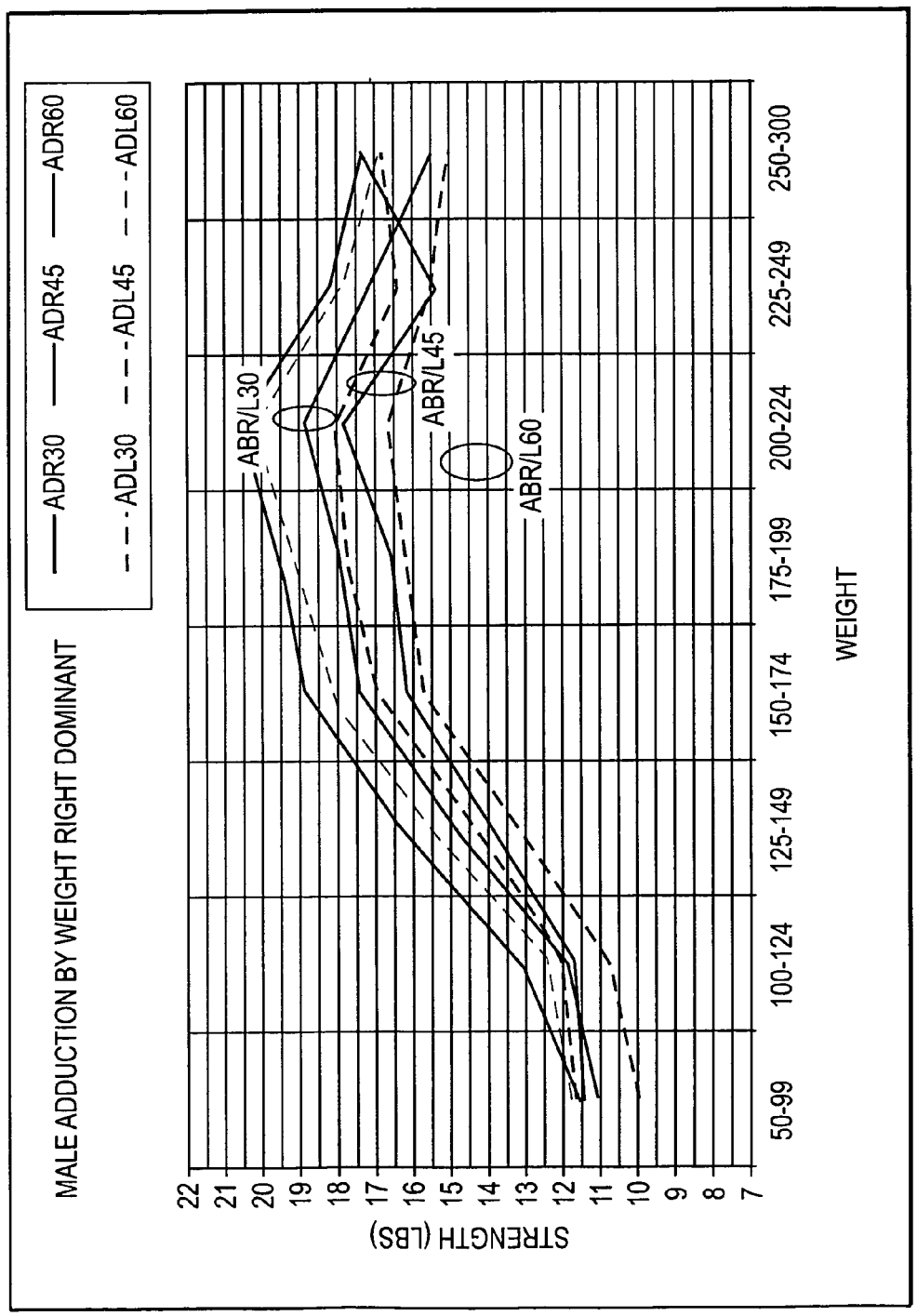
FIG. 28 is a data chart showing right dominant male adduction strength by weight at 30, 45 and 60 degree positions.
Figure 29:
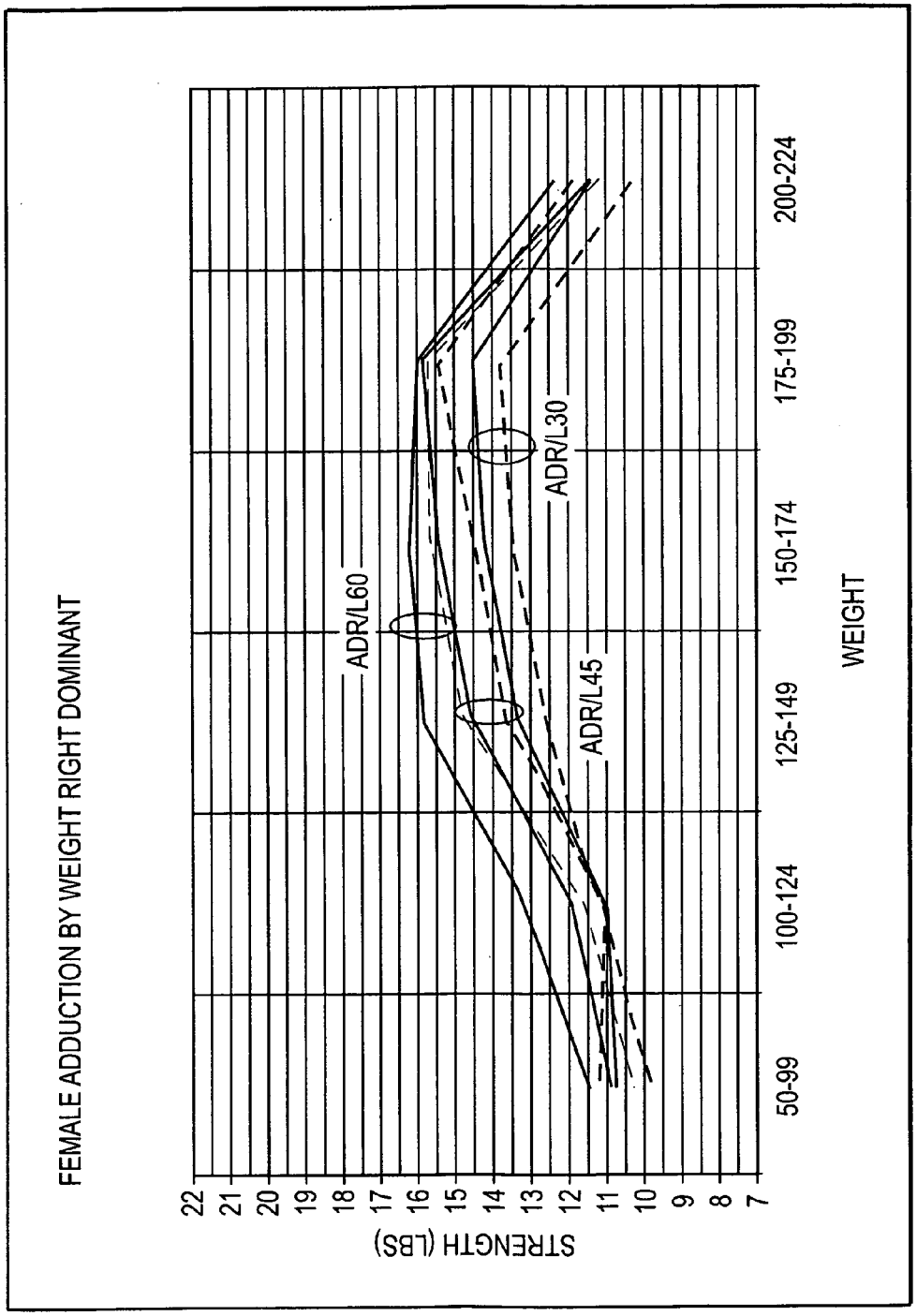
FIG. 29 is a data chart showing right dominant female adduction strength by weight at 30, 45 and 60 degree positions.

If adduction data is examined by weight, a similar pattern emerges. For males there is a steady increase by weight class, leveling off at 225 lbs with 20.5 pounds of force. There is little variation between right and left hand. As the abduction setting increases from 30 to 45 to 60 degrees, the adduction strength increases (FIG. 28). Females have the same curve as males, but the curve is much flatter and levels off at 180 lbs with 16.2 pounds of force (FIG. 29).

Figure 30:
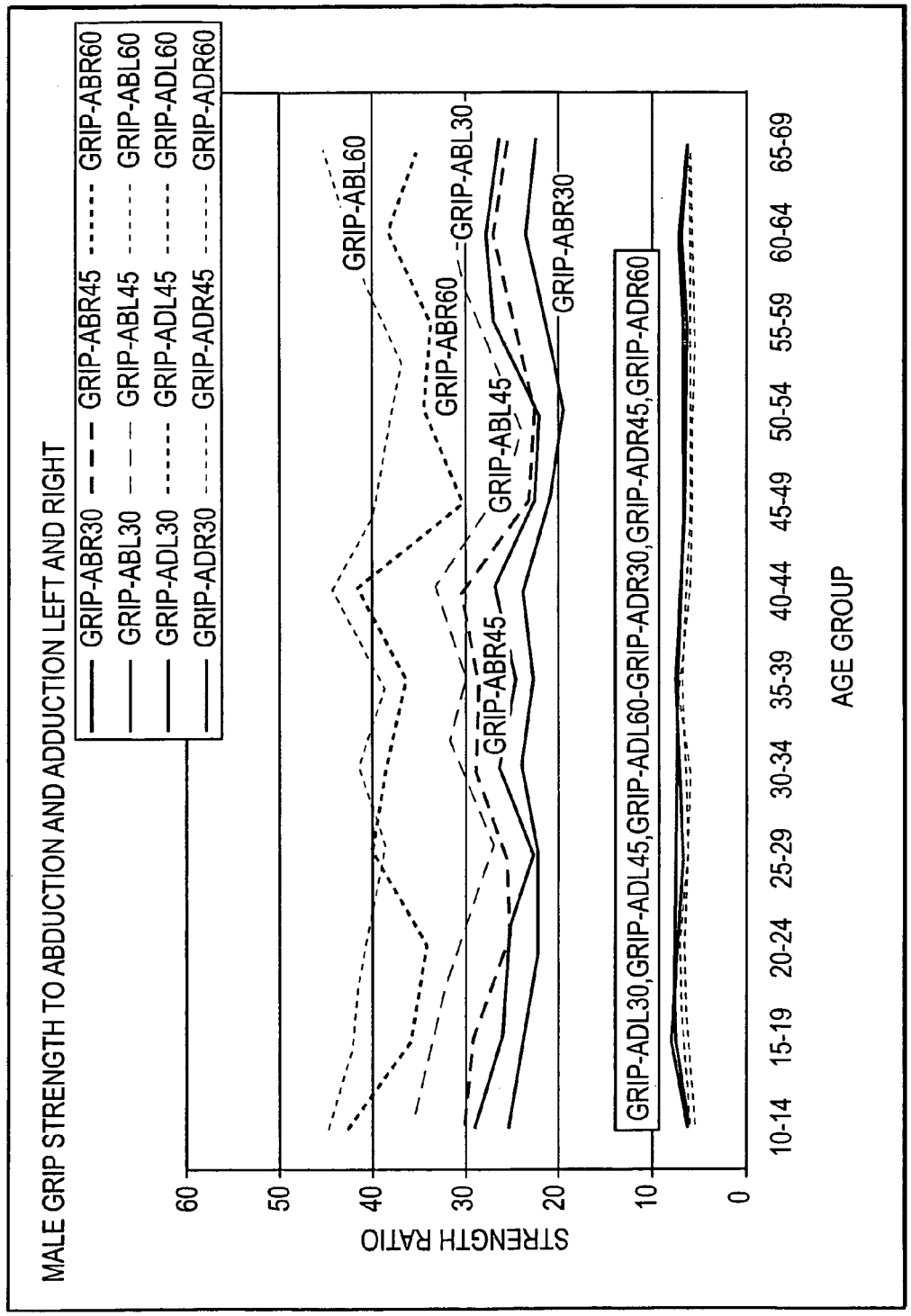
FIG. 30 is a data chart showing the ratio of male grip strength to abduction strength by age at 30, 45 and 60 degree positions.

It is instructive to correlate adduction and abduction to grip strength. The ratio of grip to adduction is linear, and age and abduction angle independent. The relationship to abduction fluctuates with age, varies between the right hand and left hand, and abduction angle. The pattern applies to both males and females (FIG. 30).

This data supports the study of correlation coefficients. There is a low correlation between adduction/abduction and grip, and between adduction/abduction and age and weight. There is a moderate correlation between adduction/abduction and right and left grip. Finally, there is a moderate to high correlation between right and left hand adduction/abduction (FIG. 31).

The many features and advantages of embodiments of the present invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A system for measuring muscle strength of a human thumb, comprising:
   a first structure contacting at least a portion of a back side of the hand;
   a second structure contacting at least a portion of a palm of the hand, said first and second strictures configured to adjustably secure the hand in a substantially fixed position and configured to secure the band in a substantially neutral position in the pronation-supination plane;
   a ring for receiving a thumb and configured so that the thumb is positioned substantially at the inter-phalangeal joint;
   a load cell comprising electronics to record a force generated by the thumb; and
   a mechanical assembly linking said ring and said load cell to transmit the forces from said ring to said load cell, wherein said mechanical assembly comprises a threaded shaft and a nut, and said ring is configured to transmit the force generated by the thumb to said threaded shaft and said nut.

2. The system according to claim 1, wherein said mechanical assembly further comprises a beam positioned substantially perpendicular to said threaded shaft, said beam transmitting the load from said threaded shaft to said load cell.

3. The system according to claim 1, further comprising a knob for rotating said threaded shaft to adjust the position of said nut on said threaded shaft, and adjusting the position of the ring to receive the thumb such that different forces are generated by the thumb corresponding to different positions of the ring responsive to said knob being adjusted.

4. The system according to claim 1, wherein said second structure is in a substantially fixed position.

5. The system according to claim 1, wherein said first structure is movable to secure the hand in the substantially fixed position.

6. The system according to claim 1, further comprising:
   a push plate;
   at least one push rod contacting said push plate and said first structure;
   a bolt secured to said first structure; and
   a handle threaded to negotiate said bolt, wherein upon rotating said handle in a first direction, said push plate, said at least one push rod and said second structure move in a direction to adjustably secure the hand in the substantially fixed position.

7. The system according to claim 1, wherein said electronics provides the capability to: a) display and record forces in at least one of metric end English units; b) display and record a peak force; c) continuously display, update and record forces generated by the thumb; and d) reset the system prior to a next exertion of force by the thumb.

8. The system according to claim 1, further comprising a connection whereby data recorded by said system can be transmitted to a computing device.

9. A system for measuring muscle strength of the human thumb, comprising:
   means for contacting at least a portion of a back side of the hand;
   means for contacting at least a portion of a palm of the hand, at least one of said means for contacting the back side and said means for contacting the palm configured to adjustably secure the hand in a substantially fixed position and for securing the hand in a substantially neutral position in the pronation-supination plane;
   means for receiving a thumb and for positioning the thumb substantially at the inter-phalangeal joint;
   means for recording a force generated by the thumb; and
   means for linking said ring and said load cell to transmit the force from said ring to said load cell.

10. A system for measuring muscle strength of the human thumb, comprising:
    a first plate contacting at least a portion of a back side of the hand;
    a second plate contacting at least a portion of a palm of the hand, said first and second plates configured to secure the hand in a substantially fixed position and configured to secure the hand in a substantially neutral position in the pronation-supination plane;
    a ring for receiving a thumb of the hand and configured so that the thumb is positioned substantially at the inter-phalangeal joint;
    a load cell comprising electronics to record a first force generated by the thumb moving in at least a first direction and to record a second force generated by the thumb moving in at least a second direction; and
    a mechanical assembly linking said ring and said load cell to transmit the force from said ring to said load cell.

11. A system for measuring muscle strength of a human thumb, comprising:
    a clamping apparatus to adjustably secure a hand in a substantially fixed position;
    a structure for receiving a thumb of the hand while the hand is in the substantially fixed position and for securing the hand in a substantially neutral position in the pronation-supination plane and for positioning the thumb substantially at the inter-phalangeal joint;
    a force measuring device to record a force generated by the thumb in abduction and adduction directions; and
    a mechanical assembly transmitting the force generated by the thumb to said force measuring device.

12. The system according to claim 11, wherein said force measuring device continuously records forces generated by the thumb over a finite period of time.

13. The system according to claim 11, wherein said structure is adjustable with respect to the hand when the hand is in the substantially fixed position.

14. A method for measuring muscle strength of a human thumb, comprising:
    adjustably securing a hand in a substantially fixed position comprising a substantially neutral position in the pronation-supination plane;
    placing a thumb of the hand substantially at the inter-phalangeal joint in a structure that enables the thumb to generate a measurable force in abduction and adduction directions; and
    recording the force in the abduction and the adduction directions.

15. The method according to claim 14, further comprising:
    providing electronics to record the force generated by the thumb; and
    providing a mechanical assembly linking the structure to the electronics to transmit the force from the structure to the electronics.

16. The method according to claim 14, wherein the thumb can move in at least a first direction and a second direction, and said recording the force includes recording the force in abduction and adduction directions responsive to separate movements of the thumb in the first and second directions.

17. The method according to claim 14, further comprising the step of adjusting the position of at least a portion of the structure with respect to the hand.

18. The method according to claim 14, further comprising the steps of:
a) displaying the force in at least one of metric end English units;
b) displaying and recording a peak force generated by the thumb; and
c) continuously displaying, updating and recording forces generated by the thumb.

19. The method according to claim 14, wherein the force is recorded by a first system, and further comprising the step of:
transmitting the recorded force to a second system.

20. A system for measuring muscle strength of a thumb or a finger of a hand, comprising:
a securing apparatus to adjustably secure a hand in a substantially fixed position;
a structure, connected to said securing apparatus, to receive the thumb or finger of the hand while the hand is in the substantially fixed position via said securing apparatus and configured to secure the hand in a substantially neutral position in the pronation-supination plane, and configured so that the thumb is positioned substantially at the inter-phalangeal joint;
a force measuring and recording device, responsively connected to said structure, to measure first and second forces generated by the thumb or finger in said structure in abduction and adduction directions respectively, and record the first and second forces to be used in at least one of diagnostic and therapeutic treatment of the thumb or finger.

21. The system according to claim 20, wherein a quantitative measure of forces generated in pure palmar thumb adduction and abduction to serve as an adjunct to grip and pinch strength in the following conditions:
osteo-arthritis pre-operation and post-operation;
rheumatoid arthritis pre-operation and post-operation;
thumb reconstruction after trauma;
reconstruction of congenital differences;
following tendon transfer surgery; and/or
following tumor resection and reconstruction.

22. The system according to claim 20, wherein said system significantly, substantially and/or completely isolates one or more muscles that are enervated by the motor branch of the median nerve or terminal motor branches of the ulnar nerve.

23. A method of measuring muscle strength of a thumb or a finger of a hand, comprising at least one of the sequential, non-sequential and sequence independent steps of:
adjustably securing the hand in a substantially fixed position comprising a substantially neutral position in the pronation-supination plane;
receiving the thumb or the finger of the hand in a force measuring device and positioning the thumb substantially at the inter-phalangeal joint;
measuring the force generated by the thumb or the finger in the adduction directions;
transmitting the force generated by the thumb or the finger to be used in at least one of diagnostic and therapeutic treatment of the thumb or finger; and
correlating the force with respect to at least one of age, weight, hand dominance and grip strength.

24. The method according to claim 23, wherein a quantitative measure of forces generated in pure palmar thumb adduction and abduction serve as an adjunct to grip and pinch strength in the following conditions:
osteo-arthritis pre-operation and post-operation;
rheumatoid arthritis pre-operation and post-operation;
thumb reconstruction after trauma;
reconstruction of congenital differences;
following tendon transfer surgery; and/or
following tumor resection and reconstruction.

25. The method according to claim 23, wherein one or more muscles that are enervated by the motor branch of the median nerve are significantly, substantially and/or completely isolated.

26. The method according to claim 23, wherein said correlating step further comprises at least one of the steps of:
correlating at least one of adduction and abduction with grip;
correlating at least one of adduction and abduction with age and weight,
correlating at least one of adduction and abduction with right and left grip; and
correlating at least one of adduction and abduction with right and left hand.

* * * * *